US012744108B2

(12) United States Patent
Banavar et al.

(10) Patent No.: US 12,744,108 B2
(45) Date of Patent: Sep. 22, 2026

(54) COMPUTER SYSTEMS AND METHODS FOR INFERRING SCORES FOR HEALTH METRICS

(71) Applicant: Viome Life Sciences, Inc., Bellevue, WA (US)

(72) Inventors: Guruduth S. Banavar, Pelham Manor, NY (US); Helen Messier, Cupertino, CA (US); Thomas Fabian, Denver, CO (US); Alla Perlina, San Diego, CA (US); Harry Joel Tily, New York, NY (US); Matteo Rinaldi, New York, NY (US)

(73) Assignee: Viome Life Sciences, Inc., Bellevue, WA (US)

( * ) Notice: Subject to any disclaimer, the term of this patent is extended or adjusted under 35 U.S.C. 154(b) by 1384 days.

(21) Appl. No.: 17/049,906

(22) PCT Filed: Apr. 22, 2019

(86) PCT No.: PCT/US2019/028590
§ 371 (c)(1),
(2) Date: Oct. 22, 2020

(87) PCT Pub. No.: WO2019/209753
PCT Pub. Date: Oct. 31, 2019

(65) Prior Publication Data

US 2021/0233615 A1 Jul. 29, 2021

Related U.S. Application Data

(60) Provisional application No. 62/661,063, filed on Apr. 22, 2018.

(51) Int. Cl.

| | |
|---|---|
| ***G16B 40/00*** | (2019.01) |
| ***A61K 35/00*** | (2006.01) |
| ***A61K 35/741*** | (2015.01) |
| ***G06N 20/00*** | (2019.01) |
| ***G16B 5/20*** | (2019.01) |
| ***G16H 20/60*** | (2018.01) |
| ***G16H 40/67*** | (2018.01) |
| ***G16H 50/20*** | (2018.01) |
| ***G16H 50/30*** | (2018.01) |
| ***G16H 50/70*** | (2018.01) |

(52) U.S. Cl.
CPC ............ *G16B 40/00* (2019.02); *A61K 35/741* (2013.01); *G06N 20/00* (2019.01); *G16B 5/20* (2019.02); *G16H 20/60* (2018.01); *G16H 40/67* (2018.01); *G16H 50/20* (2018.01); *G16H 50/30* (2018.01); *G16H 50/70* (2018.01); *A61K 2035/115* (2013.01)

(58) Field of Classification Search
CPC .......... G16B 40/00; G16B 5/20; G16B 20/00; G16B 40/20; G16B 40/30; A61K 35/741; A61K 2035/115; G06N 5/04; G06N 20/00; G16H 10/40; G16H 10/60; G16H 20/60; G16H 40/67; G16H 50/20; G16H 50/30; G16H 50/70; C12Q 2600/112; C12Q 2600/118; C12Q 2600/16; C12Q 1/689; C12Q 1/68
See application file for complete search history.

(56) References Cited

U.S. PATENT DOCUMENTS

| | | | | |
|---|---|---|---|---|
| 5,966,712 | A | 10/1999 | Sabatini et al. | |
| 8,403,847 | B2 * | 3/2013 | Rothman | G16H 50/30 600/300 |
| 9,898,574 | B2 * | 2/2018 | Yoshida | G16B 40/20 |
| 2003/0091964 | A1 | 5/2003 | Yeager | |
| 2009/0275002 | A1 | 11/2009 | Hoggle | |
| 2011/0053121 | A1 | 3/2011 | Heaton | |
| 2011/0091842 | A1 | 4/2011 | Dugan | |
| 2011/0166881 | A1 | 7/2011 | Brazzo et al. | |
| 2011/0208617 | A1 | 8/2011 | Weiland | |
| 2013/0157233 | A1 | 6/2013 | Leville | |
| 2013/0216982 | A1 | 8/2013 | Bennett et al. | |
| 2015/0079551 | A1 | 3/2015 | Egan | |
| 2015/0294593 | A1 | 10/2015 | Schoen et al. | |
| 2015/0294594 | A1 | 10/2015 | Pacione et al. | |

(Continued)

FOREIGN PATENT DOCUMENTS

| | | | |
|---|---|---|---|
| WO | 2015027057 | A1 | 2/2015 |
| WO | 2017093337 | A1 | 6/2017 |

(Continued)

OTHER PUBLICATIONS

Chen L. Gene expression profiling gut microbiota in different races of humans. Scientific Reports 6: 23075, pp. 1-11. (Year: 2016).*
Kavakiotis I. Machine learning and data mining methods in diabetes research. Computational and Structural Biotechnology Journal 15: 104-116. (Year: 2017).*
Calisir D. An automatic diabetes diagnosis system based on LDA-Wavelet support vector machine classifier. Expert Systems With Applications 38: 8311-8315. (Year: 2011).*
Wingfield B. A metagenomic hybrid classifier for paediatric inflammatory bowel disease. 2016 International Joint Conference on Neural Networks (IJCNN), pp. 1083-1089. (Year: 2016).*

(Continued)

*Primary Examiner* — Olivia M. Wise
*Assistant Examiner* — Robert J. Kallal
(74) *Attorney, Agent, or Firm* — Morgan, Lewis & Bockius LLP

(57) ABSTRACT

Provided herein are computer systems and method for producing models that infer health scores for health metrics for a subject. A first learning algorithms is trained using raw feature data stored in computer memory to build a first model that infers feature cluster scores for each of a plurality of feature clusters in a feature group. A second learning algorithms is trained using the inferred feature cluster scores stored in computer memory to build a second model that infers a heath score for a health metric.

24 Claims, 6 Drawing Sheets

(56) References Cited

U.S. PATENT DOCUMENTS

| | | | |
|---|---|---|---|
| 2015/0371553 | A1 | 12/2015 | Vento |
| 2016/0030127 | A1 | 2/2016 | Choi et al. |
| 2016/0035248 | A1 | 2/2016 | Gibbs |
| 2016/0098942 | A1 | 4/2016 | Messier |
| 2016/0140869 | A1 | 5/2016 | Kuwahara et al. |
| 2016/0166195 | A1 | 6/2016 | Radecka et al. |
| 2016/0232311 | A1 | 8/2016 | Segal et al. |
| 2016/0253922 | A1 | 9/2016 | Kremen et al. |
| 2016/0263166 | A1 | 9/2016 | Elinav et al. |
| 2016/0379520 | A1 | 12/2016 | Borel et al. |
| 2017/0262948 | A1 | 9/2017 | Bhatt et al. |
| 2017/0286619 | A1 | 10/2017 | Apte et al. |
| 2018/0122510 | A1 | 5/2018 | Apte et al. |
| 2018/0240359 | A1 | 8/2018 | Hujsak |
| 2018/0261329 | A1 | 9/2018 | Blander et al. |
| 2019/0142875 | A1 | 5/2019 | Elinav et al. |
| 2019/0251861 | A1 | 8/2019 | Wolf et al. |
| 2020/0066181 | A1 | 2/2020 | Hadjigeorgiou et al. |
| 2021/0004591 | A1 | 1/2021 | Bellaish et al. |
| 2021/0332418 | A1 | 10/2021 | Vuyisich et al. |
| 2021/0398449 | A1 | 12/2021 | Banavar et al. |
| 2022/0102000 | A1 | 3/2022 | Segal et al. |
| 2022/0130276 | A1 | 4/2022 | Banavar et al. |
| 2022/0335852 | A1 | 10/2022 | Banavar et al. |
| 2022/0335853 | A1 | 10/2022 | Banavar et al. |

FOREIGN PATENT DOCUMENTS

| | | | | |
|---|---|---|---|---|
| WO | 2017100688 A1 | 6/2017 | | |
| WO | WO-2018027179 A1 * | 2/2018 | ............. | A61P 29/00 |
| WO | 2018036503 A1 | 3/2018 | | |
| WO | 2018160899 A1 | 9/2018 | | |
| WO | 2018237209 A1 | 12/2018 | | |
| WO | 2019209753 A1 | 10/2019 | | |
| WO | 2020051559 A1 | 3/2020 | | |
| WO | 2020076874 A1 | 4/2020 | | |
| WO | 2020168015 A1 | 8/2020 | | |

OTHER PUBLICATIONS

Banavar et al. "The New Era of A1 will Revolutionize our Wellness," Proceedings of the 8th Balkan Conference of Informatics, Sep. 20, 2017, pp. 2-2.

Halfvarson et al. "Dynamics of the Human Gut Microbiome in Inflammatory Bowel Disease," Nat Microbiol, Feb. 13, 2017, vol. 2, pp. 1-15.

International Search Report and Written Opinion for International Patent Application No. PCT/US2019/028590 mailed on Jul. 23, 2019, 23 pages.

Lechatlier et al. "Richness of Human Gut Microbiome Correlates with Metabolic Markers," Nature, Aug. 28, 2013, vol. 500, No. 7464, pp. 541-546.

Korem, T. et al. Bread affects clinical parameters and induces cut microbiome-associated personal glycemic responses, Cell Metabolism, vol. 25, No. 6, Jun. 1, 2017; pp. 1243-1253.

Supplementary Partial European Search Report for EP20755298 dated Oct. 5, 2022, 24 pages.

US Office Action—Non-Final Rejection for U.S. Appl. No. 17/850,818 dated Dec. 20, 2022, 10 pages, Co-Owned.

Breitwieser, Florian, et al. "A review of methods and databases for metagenomic classification and assembly," Briefings in Bioinformatics, vol. 20, Issue 4, Jul. 2019, pp. 1125-1136, doi.org/10.1093/bib/bbx120, Published: Sep. 23, 2017.

European Search Report for Application No. 19857515, dated May 6, 2022, 8 pages (Dated of Completion Apr. 27, 2022).

European Search Report for Application No. 19870574 dated May 23, 2022, 10 pages.

Franzosa et al. "Sequencing and beyond: integrating molecular 'omics' for microbial community profiling" Nature Reviews Microbiology. Apr. 27, 2015 (Apr. 27, 2015) vol. 13, p. 360-372.

Gurry, et al., "Predictability and Persistence of Prebiotic Dietary Supplementation in a Healthy Human Cohort", Scientific Reports, Aug. 23, 2018, vol. 8, 12699 (pp. 1-13).

Hatch, A et al. A Robust Metatranscriptomic Technology for Population-Scale Studies of Diet, Gut Microbiome, and Human Health. International Journal of genomics. Oct. 1, 2019, vol. 2019, No. 1718741; pp. 1-9; entire document; DOI: 10.1155/2019/1718741.

International Search Report and Written Opinion dated Jun. 26, 2020, for PCT application No. PCT/US2020/018013.

International Search Report and Written Opinion for Application No. PCT/US19/55270, dated Jan. 2, 2020, 11 pages.

International Search Report and Written Opinion for PCT/US19/50102, dated Jan. 9, 2020, 15 pages.

Mendes-Soares, et al., "Assessment of a Personalized Approach to Predicting Postprandial Glycemic Responses to Food Among Individuals Without Diabetes", JAMA Network Open, Feb. 8, 2019, vol. 2, No. 2, e188102 (pp. 1-13).

Shi, Yanmei et al. Integrated metratranscriptomic and metagenomic analyses of stratified microbial assemblages in the open ocean, The ISME Journal (2011) 5, 999-1013 (Supplemental Materials).

Supplementary European Search Report for EP20755298 dated Jan. 9, 2023; date of completion Sep. 23, 2022, 22 pages.

Supplementary European Search Report for European Application No. 19857575, dated Apr. 29, 2022, 8 pages.

Tily Hal et al.; "Gut microbiome activity contributes to individual variation in glycemic response in adults," bioRxiv, Aug. 22, 2019, XP055923516; retrieved from the internet; URL:http://www.biorxiv.org/content/biorxiv/early/2019/08/24/641019.full.pdf, 10 pages.

US, Office Action for U.S. Appl. No. 17/855,666 dated Jan. 30, 2023, 19 pages [Co-Owned].

Zeevi, et al., "Personalized Nutrition by Prediction of Glycemic Responses", Cell, Nov. 19, 2015, vol. 163, No. 5 (pp. 1079-1094).

* cited by examiner

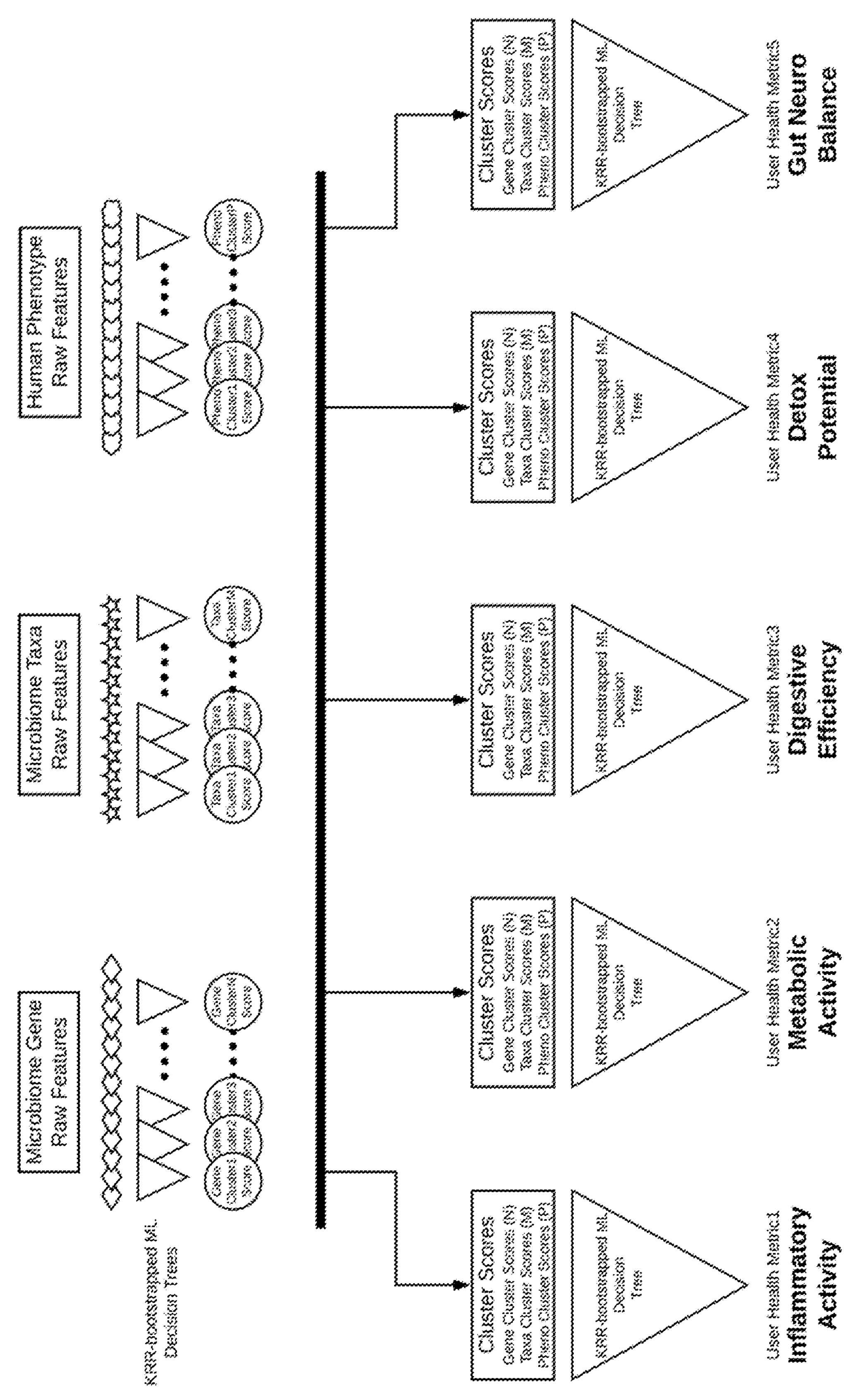
FIG. 2
Microbiome Gene Raw Features
Microbiome Taxa Raw Features
Human Phenotype Raw Features
KRR-bootstrapped ML Decision Trees
Cluster Scores
Gene Cluster Scores (N)
Taxa Cluster Scores (M)
Pheno Cluster Scores (P)
KRR-bootstrapped ML Decision Tree
User Health Metric1
Inflammatory Activity
User Health Metric2
Metabolic Activity
User Health Metric3
Digestive Efficiency
User Health Metric4
Detox Potential
User Health Metric5
Gut Neuro Balance

Note: The above comparison can be for any kind of feature cluster: gene cluster (e.g., butyrate pathway), taxa cluster (e.g., pathogens), or phenotype cluster (e.g., allergies)

COMPUTER SYSTEMS AND METHODS FOR INFERRING SCORES FOR HEALTH METRICS

REFERENCE TO RELATED APPLICATIONS

This application claims the benefit of the priority date of U.S. application 62/661,063, filed Apr. 22, 2018, the contents of which are incorporated by reference in their entirety.

STATEMENT AS TO FEDERALLY SPONSORED RESEARCH

None.

THE NAMES OF THE PARTIES TO A JOINT RESEARCH AGREEMENT

None.

SEQUENCE LISTING

None.

BACKGROUND

Methods for the collection of large amounts of data about analytes from subjects allows the creation of large data sets from which health states of the subject can be inferred. Tools such as high throughput sequencers and LC-MS quadrupole mass spectrometers are being used to generate information at the system ("-omic") level, for example, genomic, transcriptomic, proteomic and metabolomic data. Furthermore, the analysis of these analytes in the microbiome of a subject results in the collection of metadata sets of similar information across both host and different microorganisms. The character of a person's microbiome is believed to be associated with health.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIG. 2 shows an exemplary process for generating computer models for inferring a health score for a health metric. In this figure, the health metrics identified include inflammatory activity, metabolic fitness (metabolic activity), digestive efficiency, detox potential and gut neuro balance. The figure shows two main parts of the process. In the first part, shown above the solid line, a data set is provided comprising data for raw features for a plurality of different feature groups, in this case microbiome gene raw features, microbiome taxa raw features and human phenotype raw features. The features are depicted as diamonds, stars or clouds, respectively. A person skilled in the art (e.g., an expert) labels subjects, e.g., by partial order ranking for each of a plurality of feature clusters. A machine learning algorithm is trained on this data to infer feature cluster scores for each feature cluster. In a second part, shown below the solid line, a person skilled in the art (e.g., an expert) labels subjects, e.g., by a partial rank order of each subject based on the cluster scores. A machine learning algorithm is trained on this information to produce a model that infers a health score for the health metric. At both stages, labeling can be informed by Knowledge Representation and Reasoning (KRR) rules. The model may be a decision tree.

SUMMARY

Figure 1:
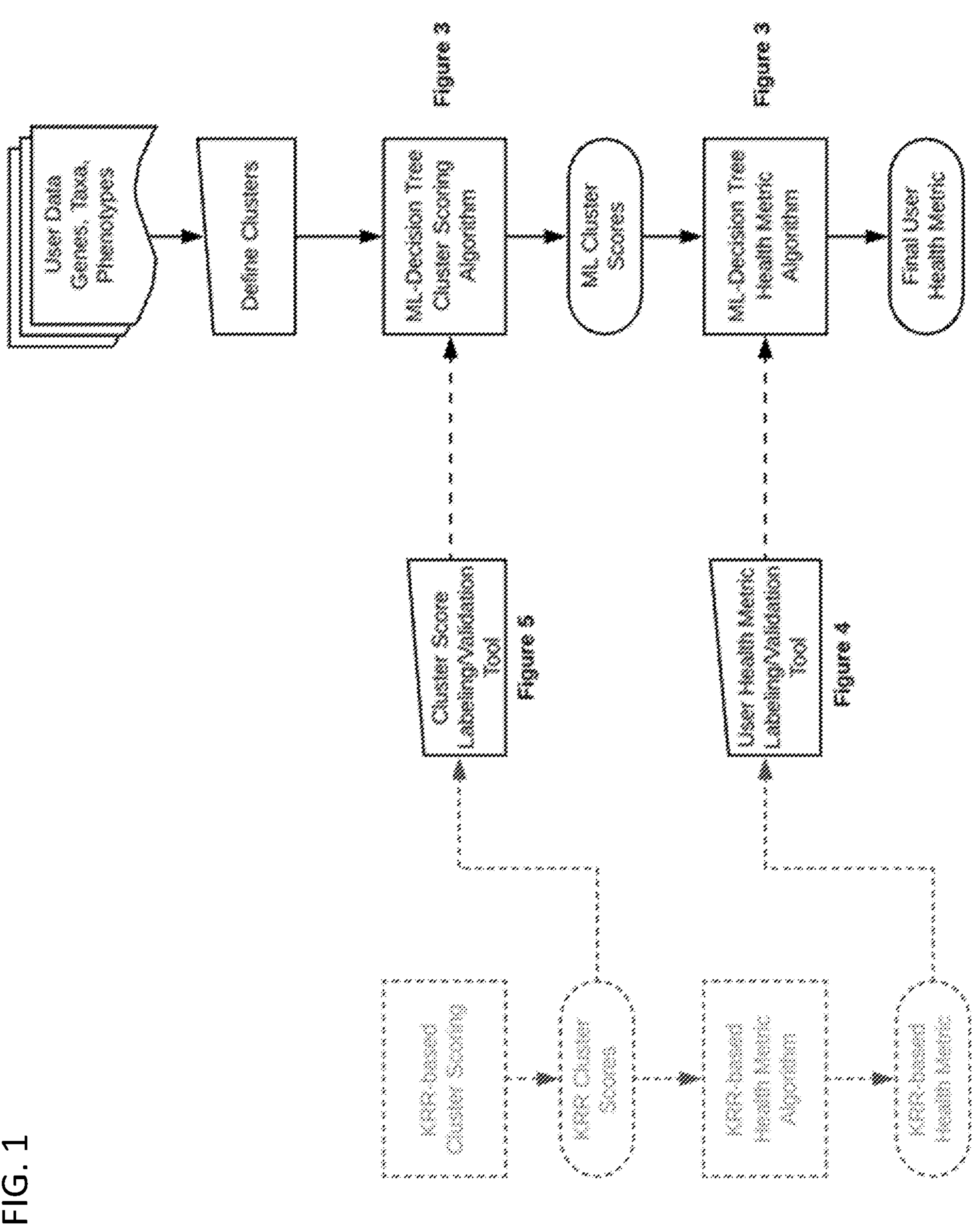
FIG. 1 shows an exemplary process for inferring a health score for a health metric for a user ("final user health metric"). User data from, typically, a plurality of different feature groups (e.g., gene expression, taxa amounts and phenotypes) are collected from a plurality of subjects. From this data, feature clusters are defined. Feature clusters are collections of features relating to some aspect relevant to the health metric. For each data cluster a label is assigned, typically by a person skilled in the art (e.g., an expert) (cluster score labeling/validation tool). A machine learning algorithm (ML-decision tree cluster scoring algorithm) is trained to infer feature cluster scores. For each subject, one or more health labels are assigned, again, typically by a person skilled in the art (e.g., an expert) (user health metric labeling/validation tool). A machine learning algorithm (ML-decision tree cluster scoring algorithm) uses the labeled cluster score data set to generate a health score (final user health metric). Labeling can be informed by knowledge representation and reasoning rules (KRR-based cluster scoring or KRR-based health metric algorithm) to generate cluster scores (KRR cluster scores) or scores for health metrics (KRR-based health metric).

In one aspect provided herein is a method comprising: a) receiving a biological sample from a subject; b) sequencing nucleic acids from biological sample to produce nucleic acid sequence feature data; c) collecting phenotypic feature data from the subject; d) performing classification or regression analysis on the feature data to assign cluster scores to each of a plurality of feature clusters, thereby producing feature cluster data; e) performing classification or regression analysis on the feature cluster data to infer health scores for each of one or more health metrics; and f) outputting the one or more health scores to an electronic device accessible by the subject. In one embodiment the electronic device is selected from a personal computer, a smart phone, a tablet, and a wearable computing device.

In another aspect provided herein is a method comprising: a) collecting feature data on a plurality of features from each of a plurality of different-omic categories from a subject, where in the -omic categories are selected from genomic, epigenomic, transcriptomic, proteomic, metabolomic, lipidomic, glycomic, immunomic, phenomic and exposomic; b) performing classification or regression analysis on the feature data to assign cluster scores to each of one or a plurality of feature clusters, thereby producing feature cluster data; c) performing classification or regression analysis on the feature cluster data to infer health scores for each of one or more health metrics; d) outputting the one or more health scores to an electronic device accessible by the subject.

In another aspect provided herein is a method for developing a computer model for inferring, from feature data, a health score for a health metric comprising: a) training a first machine learning algorithm on a first training data set, wherein the first training data set comprises, for each of a plurality of subjects, (1) feature data for each of a plurality of features selected from one or more feature groups and (2) feature cluster labels for each of one or a plurality of feature clusters, and wherein the first machine learning algorithm develops a first model that infers cluster scores for each of a plurality of feature clusters; b) executing the first model on a test data set comprising, for each of a plurality of subjects, feature data for the features, to produce a cluster score data set comprising, for each of the plurality of subjects in the test data set, feature cluster scores for each of the plurality of feature clusters; c) labeling each subject in the cluster score data set with a health label for the health metric to produce a second training data set; and d) training a second machine learning algorithm on the second training data set to develop a second model that infers a health score for the health metric. In one embodiment the health metric is selected from inflammatory activity, metabolic fitness, digestive efficiency, detoxification potential, and gut neuro-balance, neurological health, cardiovascular health, hormonal balance, musculoskeletal health, hepatic function, urogenital health, mitochondrial activity and immune function. In another embodiment the health score is provided as a continuous or discrete range. In another embodiment the health score is provided as a discrete range within any of 2, 3, 4, 5, 6, 7, 8, 9 or 10 categories (e.g., low, average and high). In another embodiment the subjects are human subjects. In another embodiment the feature groups comprise one or more of genomic, epigenomic, transcriptomic, proteomic, metabolomic, lipidomic, glycomic, immunomic, phenomic and exposomic. In another embodiment the feature groups comprise transcriptomic and phenomic. In another embodiment the feature data comprises microbiome feature data and phenotype feature data. In another embodiment the feature data comprises microbiome feature data and phenotype feature data. In another embodiment the feature groups comprise gene expression data, microbial taxa data and phenotypic data and the feature data includes at least: (1) data on gene expression for each of a plurality of genes in a microbiome of each subject; (2) microbiome taxa quantity data for a plurality of microbes in a microbiome of each subject; and (3) phenotypic data for a plurality of different phenotypic traits of each subject. In another embodiment the microbiome is a fecal microbiome. In another embodiment the microbiome is a blood microbiome. In another embodiment the gene expression data comprises meta-transcriptome sequence information. In another embodiment the gene expression data comprises data on expression of at least any of 10, 50, 100, 150, 200, 500, or 1000 different genes. In another embodiment the gene expression data comprises data on expression of genes involved in pathways associated with the health metric. In another embodiment the microbiome taxa data comprises data on microbes belonging to at least any of 10, 50, 100, 150, 200, 500, or 1000 different taxa. In another embodiment the taxa are species. In another embodiment the microbiome taxa data comprises data one or more groups selected from bacteria, viruses, Archaebacteria, yeast, fungi, parasites and bacteria phages. In another embodiment the phenotypic data comprises data on objectively and/or subjectively measurable traits for each subject. In another embodiment the phenotypic traits include one or more of: age, sex, weight, blood type, headaches, faintness, dizziness, insomnia, watery or itchy eyes, swollen, red or sticky eyelids, bags or dark circles under eyes, blurred or tunnel vision, not including near or far-sightedness, itchy ears, earaches, ear infections, drainage from ear, ringing in ears, hearing loss, stuffy nose, sinus problems, hay fever, sneezing attacks, excessive mucus formation, chronic coughing, gagging, need to clear throat, sore throat, hoarseness, loss of voice, swollen or discolored tongue, gums or lips, canker sores, acne, hives, rashes, dry skin, hair loss, flushing, hot flashes, excessive sweating, irregular or skipped heartbeat, rapid or pounding heartbeat, chest pain, chest congestion, asthma, bronchitis, shortness of breath, difficulty breathing, bloated feeling, nausea, vomiting, diarrhea, constipation, belching, passing gas, heartburn, intestinal/stomach pain, pain or aches in joints, arthritis, stiffness or limitation of movement, pain or aches in muscles, feeling of weakness or tiredness, binge eating/drinking, craving certain foods, excessive weight, compulsive eating, water retention, underweight, fatigue, sluggishness, apathy, lethargy, hyperactivity, restlessness, poor memory, confusion, poor comprehension, poor concentration, poor physical coordination, difficulty in making decisions, stuttering or stammering, slurred speech, learning disabilities, poor physical coordination or clumsiness, numbness or tingling in hands or feet, mood swings, anxiety, fear or nervousness, anger, irritability or aggressiveness, sadness or depression, frequent illness such as colds, frequent or urgent urination, genital itch or discharge, decreased libido and PMS. In another embodiment the phenotypic data comprises data collected from one or more wearable devices. In another embodiment the feature clusters comprise a plurality of gene clusters, a plurality of microbial taxa clusters and a plurality of phenotype clusters. In another embodiment each feature cluster of one or more feature clusters each comprises features belonging to the same feature group. In another embodiment each feature cluster of one or more feature clusters each comprises features belonging to different feature groups. In another embodiment the feature cluster labels comprise partial order cluster rankings assigned by a first person skilled in the field. In another embodiment partial order cluster rankings are informed by knowledge and representation reasoning rules based on knowledge in the field, e.g., expert knowledge. In another embodiment the cluster score is a quantity having a discrete or continuous range (e.g., a number, a degree, a level or a bucket). In another embodiment the feature data is provided by: (i) providing a biological sample from each subject comprising microbiota; (ii) sequencing nucleic acids in the biological sample to produce sequence data; and (iii) determining data for gene expression and microbiome taxa quantities using the sequence data. In another embodiment health labels comprise partial order health rankings are assigned by a second person skilled in the field. In another embodiment partial order health rankings are informed by knowledge and representation reasoning rules based on knowledge in the field, e.g., expert knowledge. In another embodiment the second computer model generates a positive health component and a negative health component and combines the components to produce the health metric. In another embodiment the health metric is inflammation, and feature clusters comprise one or more of: pro-inflammatory gene expression, pro-inflammatory taxa amounts, anti-inflammatory gene expression, anti-inflammatory taxa amounts, and intestinal barrier insufficiency gene expression and intestinal barrier insufficiency taxa amounts. In another embodiment (i) pro-inflammatory gene expression clusters comprise clusters for one or more of butyrate, lipopolysaccharide (LPS), flagella, urease, primary bile acids, and sulfide; (ii) anti-inflammatory gene expression clusters comprise clusters for one or more of butyrate and secondary bile acids; (iii) pro-inflammatory taxa clusters comprise clusters for one or more of: proteobacteria, opportunistic bacteria and pathogens; (iv) anti-inflammatory taxa clusters comprise clusters for one or more of: butyrate producers, Lactobacilli and Bifidobacteria; (v) intestinal barrier insufficiency gene expression clusters comprise clusters for one or more of butyrate, fucose, heparin sulfate, and (vi) intestinal barrier insufficiency taxa clusters comprise clusters for one or more of: *Akkermansia*, Clostridia, *Bacteroides*, and Sutterella. In another embodiment the health metric is metabolic fitness, and feature clusters comprise one or more of: (i) gene expression in pathways selected from one or more of: secondary bile acid pathway, primary bile acid pathway, butyrate pathway, methanogenesis pathway, acetate pathway, propionate pathway, branch chain amino acid pathway, long chain fatty acid metabolism pathway and long chain carbohydrate metabolic pathway; and (ii) taxa clusters selected from one or more of: *Prevotella* (genus)/*Bacteroides* (genus) ratio, *Eubacterium rectale* (species), *Eubacterium eligens* (species), *Faecalibacterium prausnitzii* (species), *Akkermansia muciniphila* (species), metabolic-related probiotic species (functional group), *Roseburia* (genus), *Bifidobacterium* (genus), *Lactobacillus* (genus), *Clostridium butyricum* (species), *Allobaculum* (genus), Firmicutes (phylum)/Bacteroidetes (phylum) ratio, Lachnospiraceae (family), Enterobacteriaceae (family), *Ralstonia pickettii* (species), *Bilophila wadsworthia* (species). In another embodiment the first and/or second machine learning algorithms use supervised methods selected from the group consisting of artificial neural networks (e.g., back propagation networks), decision trees (e.g., recursive partitioning processes, CART), random forests, discriminant analyses (e.g., Bayesian classifier or Fischer analysis), linear classifiers (e.g., multiple linear regression (MLR), partial least squares (PLS) regression, principal components regression (PCR)), mixed or random-effects models, non-parametric classifiers (e.g., k-nearest neighbors), support vector machines, and ensemble methods (e.g., bagging, boosting). In another embodiment the health metric is a number or a degree. In another embodiment the second computer model generates a positive health state component and a negative health state component and combines the components to produce the health metric. In another embodiment each of the positive health state components and negative health state components are determined from a combined gene cluster score derived from the gene cluster scores, a combined taxa cluster score derived from the taxa cluster scores and/or a combined phenotype cluster score derived from the phenotype cluster scores.

In another aspect provided herein is a method that infers a health score for a subject comprising: (a) providing a first data set comprising, for the subject, feature data for each of a plurality of features selected from one or more feature groups; (b) executing a first computer model on the first data set to assign feature cluster scores for the health metric to each of a plurality of feature clusters; (c) executing a second computer model on the feature cluster scores to infer a health score for the health metric for the subject. In one embodiment feature groups comprise transcriptome data and phenotype data. In another embodiment the health metric is selected from the group consisting of inflammatory activity, metabolic fitness, digestive efficiency, detoxification potential, and neuro-balance, neurological health, cardiovascular health, hormonal balance, musculoskeletal health, hepatic function, urogenital health, mitochondrial activity and immune function. In another embodiment the feature groups include one or more of genomic, epigenomic, transcriptomic, proteomic, metabolomic, lipidomic, glycomic, immunomic phenomic and exposomic. In another embodiment the feature groups comprise gene expression data, microbial taxa data and phenotypic data and the feature data includes at least: (1) data on gene expression for each of a plurality of genes in a microbiome of each subject; (2) microbiome taxa quantity data for a plurality of microbes in a microbiome of each subject; and (3) phenotypic data for a plurality of different phenotypic traits of each subject. In another embodiment data on microbiome taxa present is gathered by mapping sequence reads among the sequence data to a metagenomic database, e.g., a signature database, e.g., GOTTCHA or VIOMEGA. In another embodiment providing the first data set comprises: (i) providing a biological sample from each subject comprising microbiota; (ii) sequencing nucleic acids in the biological sample to produce sequence data; and (iii) determining data for gene expression and microbiome taxa quantities using the sequence data. In another embodiment the nucleic acids sequenced comprise RNA and determining gene expression comprises mapping sequence reads among the sequence data to an open reading frame (ORF) database. In another embodiment the first computer model and the second computer model are computer models as described herein. In another embodiment the second computer model generates a positive health component and a negative health component and combines the components to produce the health metric. In another embodiment the health metric is inflammation, the second computer model generates a positive inflammation component based on pro-inflammatory gene expression clusters and pro-inflammatory taxa clusters, and a negative inflammation component comprising anti-inflammatory gene expression clusters and anti-inflammatory taxa clusters. In another embodiment (i) the pro-inflammatory gene expression clusters comprise clusters for one or more of butyrate, lipopolysaccharide (LPS), flagella, urease, primary bile acids, and sulfide; and (ii) the pro-inflammatory taxa clusters comprise clusters for one or more of: proteobacteria, opportunistic bacteria and pathogens; (iii) the anti-inflammatory gene expression clusters comprise clusters for one or more of butyrate and secondary bile acids; (iv) the anti-inflammatory taxa clusters comprise clusters for one or more of: butyrate producers, Lactobacilli and Bifidobacteria. In another embodiment the method comprises receiving the first data set into computer memory over a communications network and transmitting the health score from computer memory over a communications network.

In another aspect provided herein is a method comprising: (a) providing a first data set comprising, for a subject, feature data for each of a plurality of features selected from one or more feature groups; (b) executing a first computer model on the first data set to assign cluster scores for a health metric to each of a plurality of feature clusters; (c) executing a second computer model on the cluster scores to assign to the subject a health score for the health metric; and recommending or providing an intervention for the subject based on the health metric. In one embodiment the intervention comprises administration of a prebiotic, a probiotic or a microbiome modulator. In another embodiment the intervention comprises a diet plan. In another embodiment the diet plan classifies foods into one of a plurality of groups ranked from most beneficial to least beneficial.

In another aspect provided herein is a software product comprising a computer readable medium in tangible form comprising machine executable code, which, when executed by a computer processor, determines a health score for a health metric for a subject by: (a) accessing a first data set comprising, for a subject, (1) feature data for each of a plurality of features selected from one or more feature groups and (2) feature cluster labels for each of a plurality of feature clusters; (b) executing a first computer model on the first data set to assign cluster scores for the health metric to each of a plurality of feature clusters; (c) executing a second computer model on the cluster scores to assign to the subject a health score for the health metric.

In another aspect provided herein is a computer system comprising: (a) a computer processor; (b) memory comprising a data set stored in memory, wherein the data set comprises for a subject, (1) feature data for each of a plurality of features selected from one or more feature groups and (2) feature cluster labels for each of a plurality of feature clusters; (c) computer readable medium comprising machine executable code in tangible form, which, when executed by the processor, determines a health score for a health metric by: (1) accessing the data set: (2) executing a first computer model on the data set to assign cluster scores for a health metric to each of a plurality of feature clusters; and (3) executing a second computer model on the cluster scores to assign to the subject a health score for the health metric.

In another aspect provided herein is a method comprising administering to a subject having a first, unhealthy health score for a health metric, an intervention to alter the first health score to a second, more healthy health score. In one aspect the health score is determined by a method as disclosed herein.

In another aspect provided herein is a method of intervention comprising: (a) providing a health score for a health metric for a subject determined by a method as disclosed herein, wherein; and (b) providing an intervention to produce a healthier health score.

In another aspect provided herein is a method of assessing inflammation in a subject comprising: assaying for, e.g., quantifying, nucleic acids corresponding to pro-inflammatory taxa in a gut microbiome of the subject; assaying for e.g., quantifying, nucleic acids corresponding to anti-inflammatory taxa in the gut microbiome of the subject; and assessing inflammation in the subject based on the pro-inflammatory taxa and anti-inflammatory taxa in the gut microbiome.

In another aspect provided herein is a method of reducing inflammation in a subject comprising: assaying for, e.g., quantifying, nucleic acids corresponding to pro-inflammatory taxa in a gut microbiome of the subject; assaying for e.g., quantifying, nucleic acids corresponding to anti-inflammatory taxa in the gut microbiome of the subject; assessing inflammation in the subject based on the pro-inflammatory taxa and anti-inflammatory taxa in the gut microbiome; and administering to the subject a probiotic that modulates inflammation-relevant taxa in the gut microbiome, or recommending to the subject a diet that modulates inflammation-relevant taxa in the subject's gut, or administering to the subject an anti-inflammatory agent selected based on the inflammatory taxa and anti-inflammatory taxa in the gut microbiome.

In another aspect provided herein is a method of assessing inflammation in a subject comprising: assaying for, e.g., quantifying, ribonucleic acids corresponding to pro-inflammatory microbial gene expression in a gut microbiome of the subject; and assaying e.g., quantifying, for ribonucleic acids corresponding to anti-inflammatory microbial gene expression in the gut microbiome of the subject; and assessing inflammation in the subject based on the pro-inflammatory microbial gene expression and anti-inflammatory microbial gene expression in the gut microbiome.

In another aspect provided herein is a method of reducing inflammation in a subject comprising: assaying for, e.g., quantifying, ribonucleic acids corresponding to pro-inflammatory microbial gene expression in a gut microbiome of the subject; assaying for e.g., quantifying, ribonucleic acids corresponding to anti-inflammatory microbial gene expression in the gut microbiome of the subject; assessing inflammation in the subject based on the pro-inflammatory microbial gene expression and anti-inflammatory microbial gene expression in the gut microbiome; and administering to the subject a probiotic to modulate inflammatory-relevant gene expression in the gut microbiome, or recommending to the subject a diet to modulate inflammatory-relevant gene expression in the gut microbiome, or administering to the subject an anti-inflammatory agent selected based on inflammatory-relevant gene expression in the gut microbiome.

In another aspect provided herein is a method comprising: a) training a first machine learning algorithm on a first training data set, wherein the first training data set comprises, for each of a plurality of objects, (1) feature data for each of a plurality of features and (2) a feature cluster label for each of one or a plurality of feature clusters, and wherein the first machine learning algorithm develops a first model that infers a cluster score for each of the feature clusters based on the feature data; b) executing the first model on a test data set comprising, for each of a plurality of objects, feature data for the features, to produce a cluster score data set comprising, for each of the plurality of objects in the test data set, a feature cluster scores for each of the feature clusters; c) labeling each object in the cluster score data set with a label for a categorical variable to produce a second training data set; and d) training a second machine learning algorithm on the second training data set to develop a second model that infers a label for the categorical variable.

In another aspect provided herein is a method comprising: a) collecting feature data from an object on a plurality of features divisible into one or a plurality of feature clusters; b) performing classification or regression analysis on the feature data to assign a cluster score to each of the feature clusters, thereby producing feature cluster data; and c) performing classification or regression analysis on the feature cluster data to infer a score for each of one or more categorical variables.

DETAILED DESCRIPTION

I. Introduction

Disclosed herein, among other things, are methods of making computer models to infer scores for health metrics, the use of these models to infer scores in individual subjects and methods of providing health improving interventions to subjects based on their scores. Also provided herein are compositions and systems to carry out the methods. As used herein, the terms "infer" and "inference" are used as they are understood in the field of machine learning to mean predict or classify or determine. In certain embodiments methods of making computer models involve using data sets comprising feature data and labels about subjects to train a machine learning algorithm to produce a first computer model that assigns cluster scores for feature clusters. The methods can further comprise labeling the cluster score data using the labeled cluster scores to train a machine learning algorithm to produce a second computer model that assigns a health score for a health metric. These two computer models can be used in sequence to produce health scores from raw feature data.

Accordingly, ultimate scoring based on raw feature data involves a two-step process in which, in a first step, a machine learning algorithm is taught to infer cluster labels to clusters of feature data based on cluster labels assigned by experts; and, in a second step, a machine learning algorithm is taught to infer a health score to cluster labeled data based on health labels also assigned by an expert. The methods described herein are more widely applicable to other kinds of data sets including feature data on a variety of objects or instances to ultimately infer a classification or score on any categorical variable.

II. Health Metrics

Health scores for health metrics can be developed for any subject. Subjects of health scores can be animals, including, for example, humans, nonhuman mammals, and nonhuman animals.

Computer models of this disclosure provide health scores for any health metric for which the model is developed. The health metric can be any measure of health. The term "health metric" also embraces health parameters, health indicators, health conditions and health risks. Health metrics include, without limitation, inflammatory activity, metabolic fitness, digestive efficiency, detoxification potential (ability of microbiome to detoxify the body), gut neuro-balance (impact of microbiome on the brain, e.g., by production of neurotransmitters), neurological health, cardiovascular health, hormonal balance, musculoskeletal health, hepatic function, urogenital health, mitochondrial activity, immune function, gastrointestinal health, diabetes, skin conditions and infectious disease. Health metrics also include categories that may contribute to more general categories, such as wellness, stress, anxiety, allergies, autoimmune condition, leaky gut, insulin resistance, metabolic syndrome, metabolic type, insomnia and, skin conditions.

A health metrics can be a direct or indirect indicator of a medical condition. For example, a poor metabolic fitness score may indicate diabetes. An intervention for an indirect health metric may ameliorate the person's medical condition.

Scores, both health scores and cluster scores, as described below, are quantitative measures that can have a discrete or continuous range. For example, a score can be a number, a degree, a level or bucket. A number can be a number on a scale, for example 1-10. Alternatively, the score can embrace a range. For example, ranges can be high, medium and low; severe, moderate and mild; or actionable and non-actionable. Buckets can comprise discrete numerals, such as 1-3, 4-6 and 7-10.

III. Data Generation

Data used in the creation of the models described herein typically comprise large data sets including thousands, tens of thousands, hundreds of thousands or millions of individual measurements taken from or about a subject, typically at the systems biology level. The data can be derived from one or more (typically a plurality) different biological system components. These biological system components, also referred to herein as "feature groups", include, without limitation, the genome (genomic), the epigenome (epigenomic), the transcriptome (transcriptomic), the proteome (proteomic), the metabolome (metabolomic), the organismal cellular lipid components (lipidome), organismal sugar components (glycome), the proteome and/or genome of the immune system (immunomics) component of a system, organism phenotype (phenome) and environmental exposure (exposome).

Data can include information about microbes in the subject's microbiome, e.g., gut microbiome. To the extent the data includes information from a plurality of different organisms in the microbiome, the data can be classified as meta-data, such as meta-genomic, meta-transcriptomic, meta-metabolomic, meta-proteomic and meta-epigenetic.

Data can also include phenotypic information about a subject, that is, information about objectively and/or subjectively measurable traits for a subject. Data can include lifestyle information about a subject including, for example, diet, exercise, stress, alcohol use, drug use, supplement use, and sleep patterns. Data also can include biomic, e.g., environmental, information about a subject including, for example, exposure to toxins, climate, external temperature, social interactions, location, work environment, hydration, activity level, and the like.

A. Data Sources

Biological samples can provide biomolecules belonging to any of the feature groups for analysis. Biological samples can include, without limitation, earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue (e.g., a skin biopsy), subcutaneous tissue, muscle tissue, adipose tissue, and a combination thereof.

Nucleic acids to be sequenced include nucleic acids taken from cells in the sample or extracellular nucleic acids found in a sample. For example, in the case of stool samples, cells are typically lysed and nucleic acids are isolated from the lysate. In the case of samples such as blood or urine, nucleic acids can be extracted from cells in the blood or extracellular nucleic acids may be present as so-called cell free nucleic acids, e.g. cfDNA or cfRNA.

Nucleic acids for analysis can include the transcriptome from nucleic acids from a gut microbiome sample or a blood sample. Total nucleic acids from a sample can be isolated. DNA can be removed from the sample by, for example, DNAase digestion. Remaining RNA can be treated to remove non-informative RNA's. Non-informative RNA species can include one or more of: human ribosomal RNA (rRNA), human transfer RNA (tRNA), microbial rRNA, and microbial tRNA. Non-informative RNA species can further comprise one or more of the most abundant mRNA species in a sample. For example, in a blood sample, hemoglobin and myoglobin mRNA are highly abundant species. Other common species include HFM1, PDE3A, HBB, MALAT1, ATP8/ATP6, ND4L and COX1. Noninformative RNA can be removed, for example, by the use of oligonucleotide probes directed against the RNAs. After noninformative RNA is removed the remaining RNA, in particular, mRNA, can be reverse transcribed into DNA and further processed. What a plurality of samples is being processed, the amount of nucleic acid in different samples can be normalized, for example, to contain the same amounts of nucleic acid. Results from such samples may be more comparable between the samples. Nucleic acids in different samples can be tagged with sample barcodes to enable simultaneous sequencing of nucleic acids from different samples and assignment of sequence reads to original samples based on barcodes. Methods of barcoding samples are described in, for example, WO 2018/237209, published Dec. 27, 2018 ("Systems and methods for identification of nucleic acids in a sample"). Samples from the gut, e.g., feces, provide nucleic acids from the gut microbiome. Blood samples provide both cell-based and cell-free nucleic acids. White blood cells can be isolated from blood. RNA from these samples provide information about the host metabolic function including, for example, mitochondrial function, protein and carbohydrate metabolism, etc.

Data can be from questionnaires provided to subjects, medical records, or evaluations of subjects by a health professional. Data can be from one or more wearable devices that measure and/or calculate, for example, heart rate, heart rhythm, heart rate variability (HRV), respiration, temperature, exercise (e.g., steps), sleep patterns, physical location.

B. Data Formats

Data can include measurements made on nucleic acids from a subject. This includes, for example, nucleic acid sequences reflecting meta-genomic and or meta-transcriptomic information. Such information typically requires isolation and sequencing of nucleic acids in one or more samples from the subject. Nucleic acids to be sequenced can include both DNA and RNA. Sequencing nucleic acids typically involves converting raw nucleic acids into a form compatible with a high throughput sequencer. This may include, in the case of RNA, reverse transcribing RNA into DNA. It may also include providing adapter molecules on DNA molecules adapted for function with particular DNA sequencer.

Nucleic acids can be sequenced by any methods known in the art to produce sequence reads comprising nucleotide sequences. Typically, nucleic acid sequencing is performed by high throughput sequencing. High throughput sequencing refers to the simultaneous or near simultaneous sequencing of thousands of nucleic acid molecules. High throughput sequencing is sometimes referred to as "next generation sequencing" or "massively parallel sequencing". Platforms for high throughput sequencing can be any suitable platform and include, without limitation, massively parallel signature sequencing (MPSS), Polony sequencing, 454 pyrosequencing, Illumina (Solexa) sequencing, SOLID sequencing, Ion Torrent semiconductor sequencing, DNA nanoball sequencing (Complete Genomics), Heliscope single molecule sequencing, single molecule real time (SMRT) sequencing (PacBio), and nanopore DNA sequencing (e.g., Oxford Nanopore). Raw sequence reads are typically subject to bioinformatic analysis to transform the data into a format more useful for study. For example, sequence reads may be quantified to determine absolute or relative numbers of molecules having the same nucleotide sequence or having been derived from the same gene or the same area of the genome. Sequence data can be further analyzed, for example, to determine quantitative measures (e.g., absolute or relative amounts) of microorganisms in specific categories at different taxonomic levels. This includes, for example, identification of different phyla, order, class and/or species of microorganism.

Phenotypic information can be obtained, for example, from subject responses to questionnaires, or from a chat bot that interacts with the subject through natural language conversations. Such questionnaires may gather information on traits such as age, sex, weight, blood type, headaches, faintness, dizziness, insomnia, watery or itchy eyes, swollen, red or sticky eyelids, bags or dark circles under eyes, blurred or tunnel vision (not including near or far-sightedness), itchy ears, earaches, ear infections, drainage from ear, ringing in ears, hearing loss, stuffy nose, sinus problems, hay fever, sneezing attacks, excessive mucus formation, chronic coughing, gagging, need to clear throat, sore throat, hoarseness, loss of voice, swollen or discolored tongue, gums or lips, canker sores, acne, hives, rashes, dry skin, hair loss, flushing, hot flashes, excessive sweating, irregular or skipped heartbeat, rapid or pounding heartbeat, chest pain, chest congestion, asthma, bronchitis, shortness of breath, difficulty breathing, bloated feeling, nausea, vomiting, diarrhea, constipation, belching, passing gas, heartburn, intestinal/stomach pain, pain or aches in joints, arthritis, stiffness or limitation of movement, pain or aches in muscles, feeling of weakness or tiredness, binge eating/drinking, craving certain foods, excessive weight, compulsive eating, water retention, underweight, fatigue, sluggishness, apathy, lethargy, hyperactivity, restlessness, poor memory, confusion, poor comprehension, poor concentration, poor physical coordination, difficulty in making decisions, stuttering or stammering, slurred speech, learning disabilities, poor physical coordination or clumsiness, numbness or tingling in hands or feet, mood swings, anxiety, fear or nervousness, anger, irritability or aggressiveness, sadness or depression, frequent illness such as colds, frequent or urgent urination, genital itch or discharge, decreased libido and PMS. Phenotypic information can be collected all in a single session, in several sessions involving a small number of questions at each session, and over weeks, months or years, creating a 'longitudinal' view of the subject's phenotype.

IV. Model Creation

Models are created by training machine learning algorithms on training data sets comprising data from a plurality of subjects. The machine learning algorithm can be a classification algorithm or a progression algorithm. In certain embodiments, models for inferring health scores involve using feature data in the creation of first models to infer cluster scores for each of a plurality of feature clusters in each of a plurality of cluster groups and using the cluster scores in the creation of second models to infer health scores.

In general, model building involves providing a dataset. The dataset comprises data on a plurality of objects or instances, e.g., subjects. Data for each subject is provided for each of a plurality of features, or variables that are the subject of analysis. Accordingly, data on each instance can be presented as a vector and the collection of vectors for each instance comprise the dataset. The variable to be predicted is sometimes referred to as a "categorical variable". In supervised learning a value, or label for a categorical variable for each instance can be provided as part of the dataset. So, for example, if the categorical variable is a particular indicator of health or disease, data for a subject can include as a feature a value or label for that indicator. For example, the value could be "present" or "absent".

A. Model to Infer Feature Cluster Scores

1. Features, Feature Groups and Feature Clusters

Data collected can be organized into raw features. Data for features can represent analytes or characteristics being measured or described. For example, expression levels of individual genes can be features, amounts of microorganisms belonging to specific taxonomic categories can be features, and phenotypic traits (that is, the form a phenotype takes) can be features.

Features can, in turn, be organized by feature group. As discussed above, feature groups include, for example, genomic features, epigenomic features, transcriptomic features, proteomic features, metabolomic features, lipidomic features, glycomic features, immunomic features, phenomic (phenotypic) features and exposomic features. Feature groups can be organized based on different biological system components, e.g., they can represent data of a certain type or from a common source. For example, feature groups can include, without limitation, a feature group that includes data on the gut microbiome, such as quantitative measures of categories of microbes present; data on the gut meta-transcriptome or the blood meta-transcriptome, such as quantitative measures of expression levels of various genes; data on the urine metabolome, such as quantitative measures of a variety of metabolites present; data on the subject exposome, such as quantitative measures of exposure to toxins, light and environmental temperature; and data on the subject phenotype, such as quantitative measures of any variety of phenotypic traits of a subject. Thus, groups of data on various features that are measured can be organized into feature groups, typically based on a common source for the data.

Using knowledge in the field, features are, in turn, organized into feature clusters which comprise a plurality of features. A feature cluster can include features all from the same feature group or features from different feature groups. Feature clusters are selected with reference to the particular health metric for which the model is being developed. Also, a given feature cluster may be relevant to multiple health metrics. Feature clusters can include, for example, gene expression clusters, microbial taxa clusters and phenotype clusters. Each feature cluster typically will include commonly related features. For example, a gene expression cluster can include genes belonging to a common biochemical pathway. A microbial taxa cluster can include microbes whose presence contribute to the common health metric. A phenotype cluster can include phenotypes relating to a common trait, for example, a plurality of traits that are related inflammation or that all relate to a gastrointestinal problem.

Any number of features can be grouped into a feature cluster, e.g., at least 1, at least 2, at least 5, at least 10, at least 50 or at least 100. Any number of feature clusters may be used in the determination of the health score. There may be one or more clusters used, e.g., at least 1, at least 2, at least 5, at least 10, at least 50 or at least 100. Clusters may include features for one or more feature groups, e.g., at least 1, at least 2, at least 5, at least 10, at least 50 or at least 100.

In certain embodiments, a feature cluster includes genes in a biochemical pathway and their expression levels. Biological pathways are known in the art and can be found, for example, on the web at wikipathways.org/index.php/WikiPathways, pathwaycommons.org, and proteinlounge.com/Pathway/Pathways.aspx.

So, for example, where the health metric is inflammatory activity, feature clusters associated with inflammation are selected. In a gene expression group feature cluster, gene clusters for inflammation can include, for example, genes in the butyrate pathway, genes in the secondary bile acids pathway, genes in the lipopolysaccharide biosynthesis pathway, genes in the flagella pathway, genes in the urease pathway, genes in the primary bile acids pathway and genes in the sulfide pathway. Genes in each of these pathways are known to person skilled in the art. In a microbiome taxa feature cluster, taxonomic categories for information can include, for example, butyrate producers, lactobacilli, bifidobacteria, proteobacteria, opportunistic bacteria and pathogenic bacteria and viruses. In a phenotype group cluster, phenotypes informative of inflammation can include, for example, allergy symptoms such as watery/itchy eyes, stuffy nose, swollen, red or sticky eyelids, sinus problem, sneezing attacks, hay fever, excessive mucus formation, asthma, bronchitis; musculoskeletal symptoms such as pain or aches in joints or muscles, arthritis, stiffness or limitation of movement' neurological symptoms such as headaches, insomnia, poor memory, confusion, poor comprehension, poor concentration, anxiety, fear, anger, irritability, sadness, depression; skin symptoms such as rash, dry, itchy skin, eczema, etc.

Where the health metric is metabolic fitness, feature clusters can include genes in pathways selected from the secondary bile acid pathway, primary bile acid pathway, butyrate pathway, methanogenesis pathway, acetate pathway, propionate pathway, branch chain amino acid pathway, long chain fatty acid metabolism pathway and long chain carbohydrate metabolic pathway. Taxa clusters can include *Prevotella* (genus)/*Bacteroides* (genus) ratio, *Eubacterium rectale* (species), *Eubacterium eligens* (species), *Faecalibacterium prausnitzii* (species), *Akkermansia muciniphila* (species), metabolic-related probiotic species (functional group), *Roseburia* (genus), *Bifidobacterium* (genus), *Lactobacillus* (genus), *Clostridium butyricum* (species), *Allobaculum* (genus), Firmicutes (phylum)/Bacteroidetes (phylum) ratio, Lachnospiraceae (family), Enterobacteriaceae (family), *Ralstonia pickettii* (species), *Bilophila wadsworthia* (species). Phenotypic features can include blood glucose and/or insulin measurements, body mass or body mass index, percent body fat and the like.

Where the health metric is digestive efficiency, feature clusters can include genes in pathways selected from the primary bile acid pathway, methanogenesis, putrescine production pathways, fucose metabolism pathway, urea cycle pathway, ammonia pathways. Taxa clusters can include protein fermenters, sulfide producers, any species from the super-kingdom Archaea, oral taxa, bile tolerant taxa, intestinal lining disruptors/degraders taxa. Phenotypic features can include gas (anywhere in the GI tract), bloating, intestinal pain, diarrhea, constipation, acid reflux.

2. First Training Data Set

First training data sets are used to train machine learning algorithms to generate cluster scores for the feature groups. Training datasets typically take the form of vectors comprising feature data for each of a plurality of objects. In the present case the objects typically are subject individuals, e.g., persons.

The first training sets typically include data for each of a plurality of subjects. (In the field of machine learning, each row of the vector corresponds to an "object", in this case, a subject.) For each subject, the first training data set includes data for a plurality of raw features, as described above. Furthermore, within each feature cluster the subjects are labeled with respect to the health metric for which the model is being developed. The label can be a category, such as "healthy," or "unhealthy"; or arrange such as "high", "medium", and "low". In certain embodiments the label is a partial order ranking. In such an instance subjects can be ranked for the feature cluster from highest to lowest. Labels are used by a supervised machine learning algorithm in the development of models to infer labels which may be of the same or different kind. For example, while labels in the training data can be partial order ranked, labels inferred by the machine learning algorithm may classify by a number, range or category.

The number of subjects selected should be sufficient to provide a robust model, e.g., a model with at least 60%, at least 70%, at least 80% at least 90% or at least 95% specificity (a.k.a. precision), sensitivity (a.k.a. recall) and/or positive predictive value (a.k.a. accuracy). In certain embodiments the training data set includes data from at least 10, at least 100 or at least 1000 different individuals.

a) Partial Order Ranking Based on a Feature Cluster

In partial order ranking, items are ranked highest to lowest with respect to some criterion, with the possibility of some items being tied for the same ranking. For example, ten items may be ranked with one item in first place, three items tied for 2nd-4th place, one item in 5th place, three items tied for 6th-8th place, one item in 9th place in one item in 10th place.

In one operation, based on data for features in a feature cluster, the subjects are partial order ranked from highest to lowest as characterized by the health metric. Subjects are rank ordered for the health metric based on each feature cluster. So, for example, the health metric "inflammatory activity" may include as feature clusters butyrate expression and lipopolysaccharide expression. In the dataset, for the feature cluster butyrate expression, each subject receives a partial order ranking indicating relative rank for butyrate expression. Similarly, for the feature cluster lipopolysaccharide expression, each subject receives a partial order ranking indicating relative rank for lipopolysaccharide expression.

Figure 3:
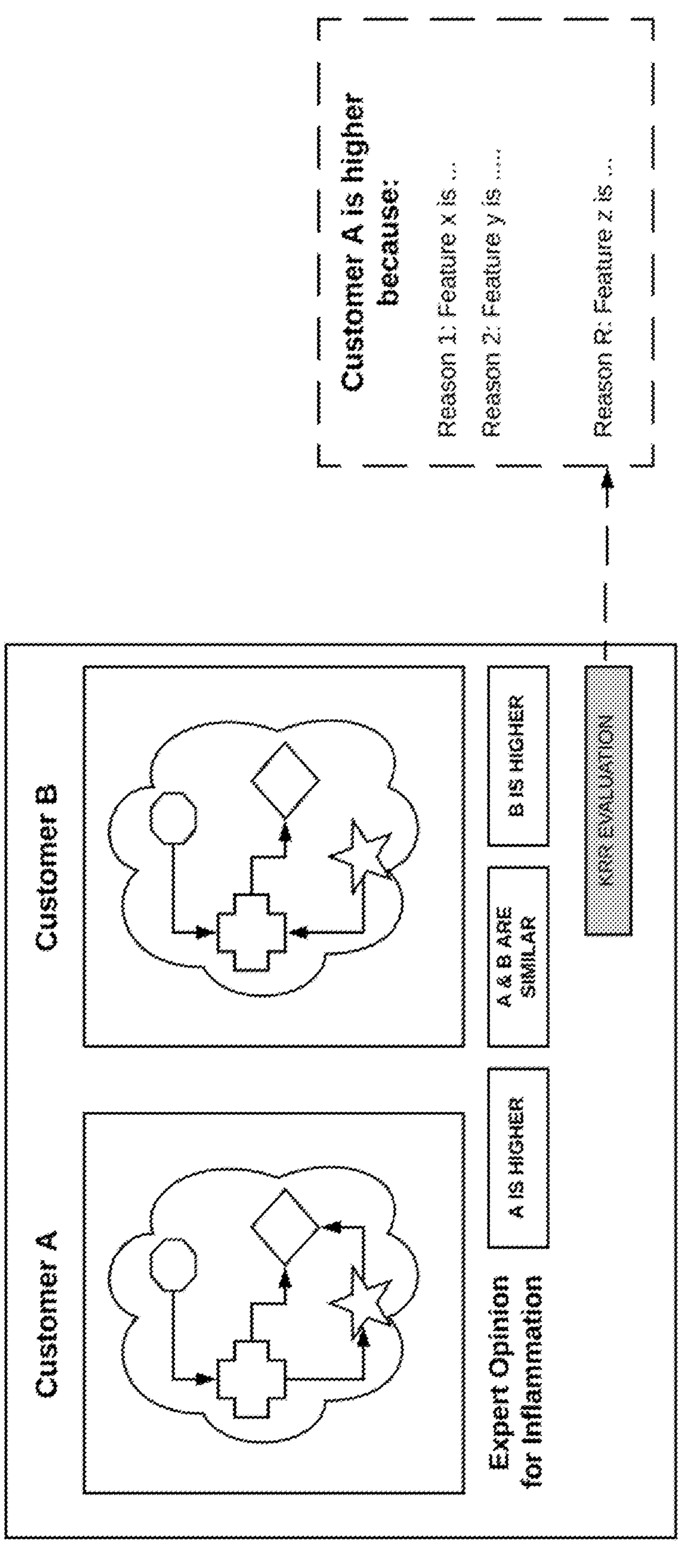
FIG. 3 shows an exemplary expert labeling tool for partial order ranking of subjects (identified here as "Customer A" and "Customer B", but not necessarily customers) based on particular feature clusters. The feature cluster comprises data for a plurality of raw features, in this case depicted by the shapes (octagon, cross, star and diamond). The person skilled in the area for which the health metric is being developed can choose the subject that the person believes ranks better on a health metric based on a comparison of cluster scores ("A is higher" or "B is higher"), or, alternatively, that the two subjects should be considered to have about the same rank ("A&B are similar"). Where the person is uncertain about which subject to choose, the decision can be given to an algorithm that applies rules developed by a person skilled in the art (e.g., an expert) ("KRR evaluation"). The KRR evaluation includes rules based on feature characteristics ("Customer A is higher because: Reason 1: Feature x is . . . Reason 2: Feature y is . . . Reason R: Feature z is . . . ")
Figure 4:
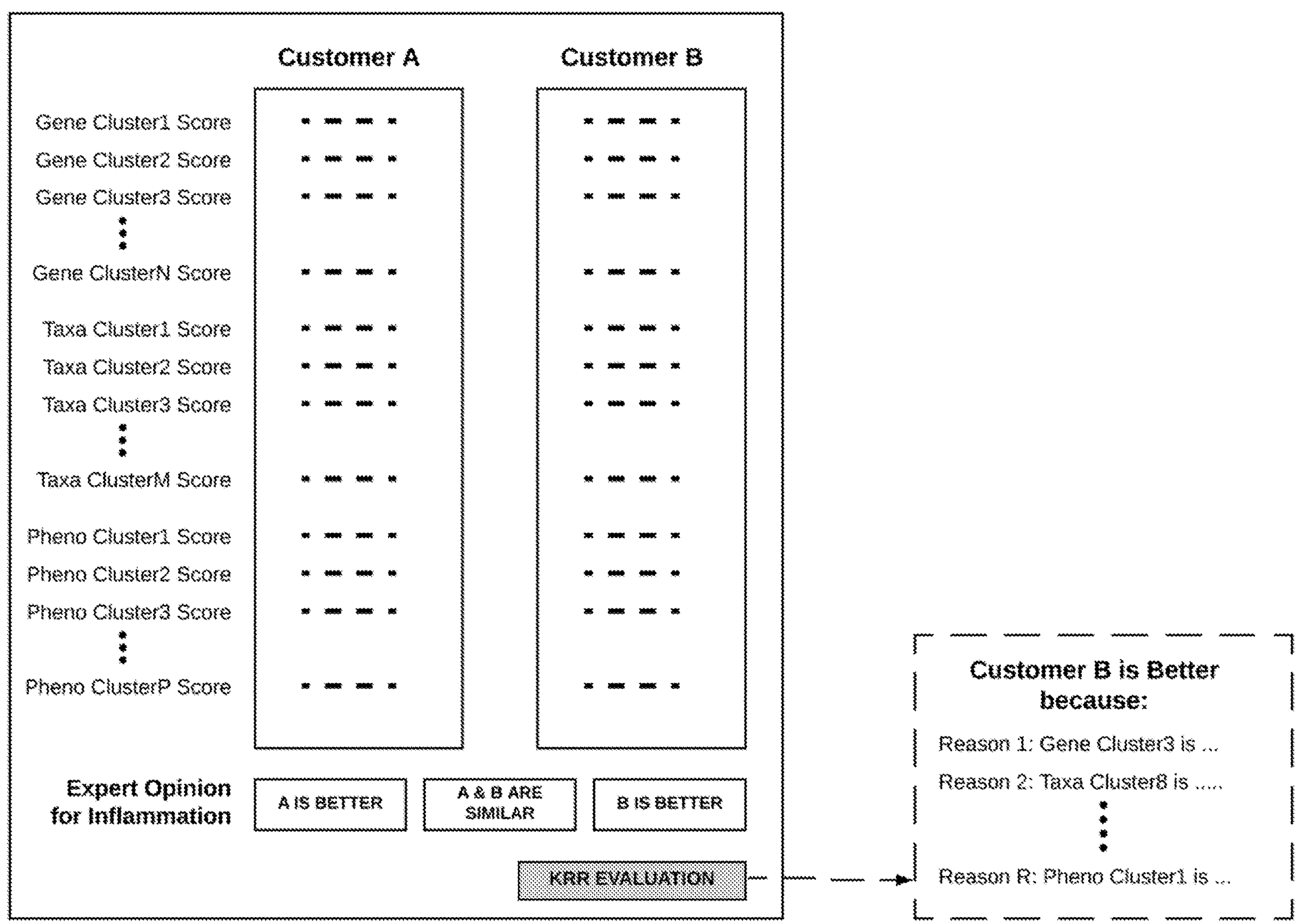
FIG. 4 shows an exemplary outline of data sets generated from data from two subjects, identified here as "Customer A" and "Customer B" for partial order ranking by a person skilled in the art (e.g., an expert). The data set comprises, for each subject, feature cluster scores for each of a plurality of feature clusters in each of a plurality of feature groups. In this case, the feature clusters are Gene Clusters (indicating pathway activity), Taxa Clusters (indicating relative amounts of groups of microorganisms) and Pheno Clusters (indicating one or more phenotypes). The person can choose the subject that the person believes ranks better on a health metric based on a comparison of cluster scores ("A is better" or "B is better"), or, alternatively, that the two subjects should be considered to have about the same rank (A&B are similar"). Where the person is uncertain about which subject to choose, the decision can be given to an algorithm that applies rules developed by a person skilled in the art (e.g., an expert) ("KRR evaluation").

Referring to FIG. 3, partial order ranking can be performed by a first person in the relevant field. The person typically will use publicly available information and their own experience to perform the ranking. Thus, for example, a person skilled in the art (e.g., an expert) may determine that higher levels of gene expression in the butyrate pathway indicate decreased levels of inflammation. This determination may be subtler, for example the person may weight expression of certain genes in the pathway more heavily than others. In certain embodiments, ranking is performed in a pairwise fashion in which the person is presented with feature data for two individuals and chooses the subject with a higher degree of the health metric. In certain cases, the person may decide that neither subject is higher or lower and that the result is a tie. In other situations, the person may determine that a decision cannot be made between the two subjects. In this case, the person may request a knowledge representation and reasoning algorithm that applies predetermined rules to make the decision.

Accordingly, a first training data set can comprise, for each of a plurality of subjects, raw feature data for a plurality of features in each of a plurality of feature groups and, for each of a plurality of feature clusters in each of the feature groups, a partial order ranking of the subject.

3. Machine Learning Algorithms

The machine learning algorithm can be any suitable supervised machine learning algorithm, parametric or non-parametric. Unsupervised machine learning methods also can be used. In supervised methods values for the categorical variable to be inferred are provided for each object in the dataset. In unsupervised methods, such values are not included in the dataset. Inference may be determined by, for example clustering data in inferring the cluster to which a subject belongs.

Machine learning algorithms include, without limitation, artificial neural networks (e.g., back propagation networks), decision trees (e.g., recursive partitioning processes, CART), random forests, discriminant analyses (e.g., Bayesian classifier or Fischer analysis), linear classifiers (e.g., multiple linear regression (MLR), partial least squares (PLS) regression, principal components regression (PCR)), mixed or random-effects models, non-parametric classifiers (e.g., k-nearest neighbors), support vector machines, and ensemble methods (e.g., bagging, boosting).

In artificial neural networks and interconnected group of nodes organized into a plurality of layers of modes. These may include an input layer one or more hidden layers and an output layer. Each node inputs may be summed e.g. based on their weights.

Support vector machines draw hyperplanes in multidimensional space to divide objects in the training dataset into categories.

4. Training a Machine Learning Algorithm to Infer Data Cluster Scores

In a subsequent operation, the first training data set is used to train a machine learning algorithm. The product of training is a cluster score model that assigns a feature cluster score for each of the feature clusters. Feature cluster scores can indicate relative position on a scale for the health metric in question. Based on the partial order ranking associated with the raw feature data for the data clusters, the machine learning algorithm learns what cluster score to assign a feature cluster.

5. Feature Cluster Score Data Sets

In a subsequent operation, the cluster score model is used to create a feature cluster score data set by inferring cluster scores for each feature cluster for each subject in a test raw data set. The test raw data set comprises data on the raw features used to train the first machine learning algorithm. The inference operation produces a second training data set that includes, for each subject in the test data set, inferred feature cluster scores for each feature cluster. This produces a cluster score data set for use in a subsequent operation.

B. Model to Infer Health Scores

In the second training operation a person skilled in the art (e.g., an expert) in the field of the health metric labels each subject for the health metric based on their cluster scores in a cluster score data set produced in the previous operation. Labeling can involve a partial order ranking of the subjects. Note that in the previous labeling involving partial order ranking, the person used raw feature data to rank subjects according to individual feature clusters. In the current instance of labeling by partial order ranking, the person uses feature cluster scores generated by the first computer model to rank subjects according to the ultimate health metric.

In this operation, the person may be the same or a different person than the one that performed the first partial order ranking. Again, partial order ranking can be performed by pairwise comparison of data for two subjects and ranking them as higher, lower or the same for the health metric based on the combined feature cluster scores. The product of the partial order ranking is a second training data set that includes for each subject the feature cluster scores and a relative rank order for the health metric.

In a subsequent operation, the second training data set is used to train a machine learning algorithm to produce a model that infers a health score for the health metric for a subject based on feature cluster scores. The machine learning algorithm used in this operation may be the same or different as the one used in the previous training operation.

Figure 5:
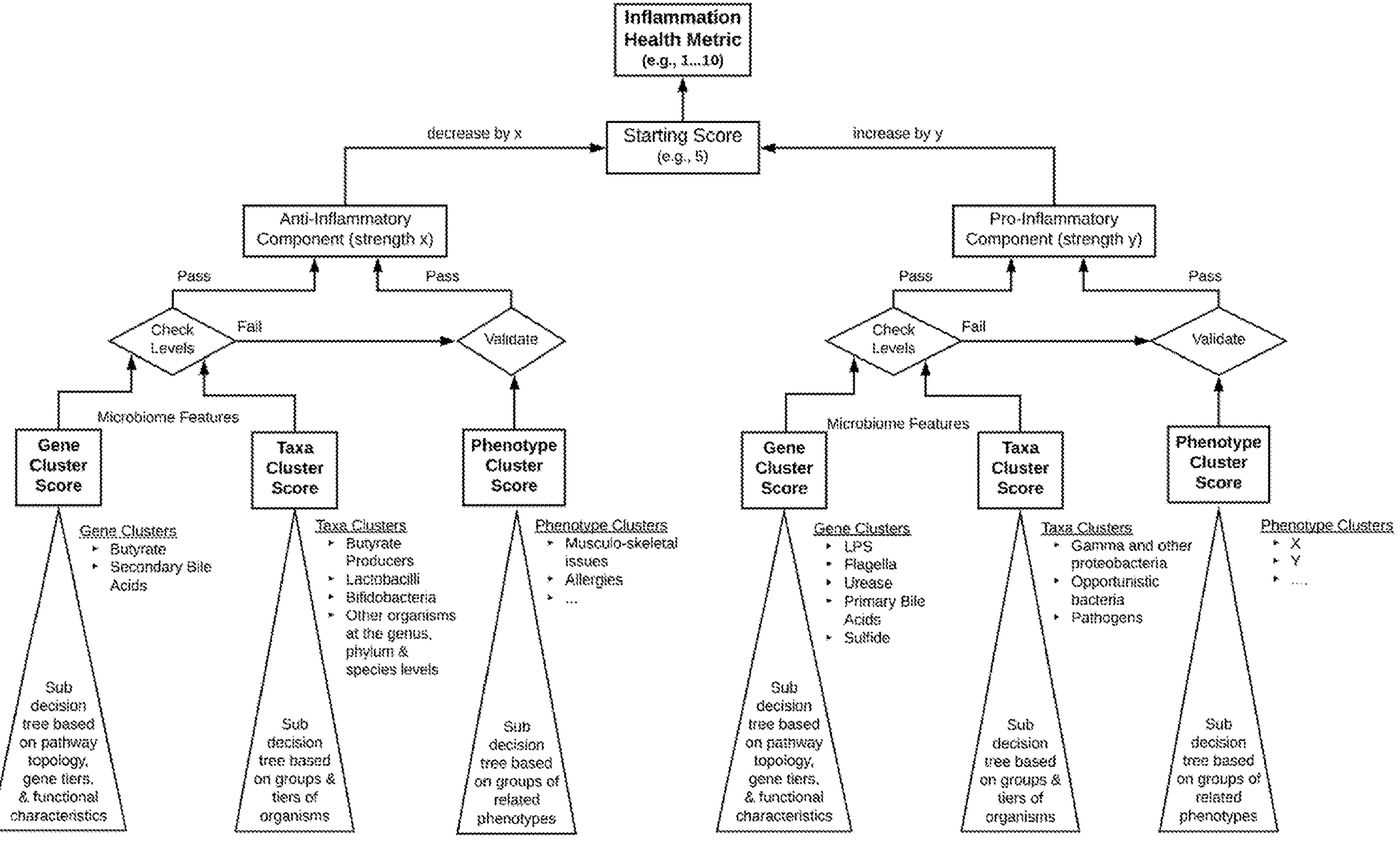
FIG. 5 shows an exemplary model, which could be machine-learnt or hand-crafted, for inferring an Inflammation Score for the health metric, Inflammation. Microbiome Gene Cluster Scores can be determined based on a sub-decision trees based on pathway topology, gene tiers and functional characteristics. Microbiome Taxa Cluster Scores can be determined based on sub-decision trees based on groups and tiers of organisms. And Phenotype Cluster Scores can be determined by sub-decision trees based on groups of related phenotypes. The model generates a single pro-inflammatory and an anti-inflammatory Cluster score for each feature group using sub decision tree pathway topologies, tiers and functions. The Gene Cluster Score and the Taxa Cluster Score for the anti-inflammatory and pro-inflammatory branches produce an anti-inflammatory or pro-inflammatory component which may be validated by the anti- or pro-inflammatory Phenotype Cluster Score. These components are then used to adjust a Starting Score toward the anti-inflammatory or pro-inflammatory directions to produce the final Score.

The second model may employ sub-decision trees to determine intermediate scores for overall feature groups, which, in turn, are used generate pro- and anti-components for the health metric. These, in turn, can be used to adjust a starting or initial score for the health metric in the pro- or anti-direction, depending on relative weights of the components. So, for example, referring, e.g., to FIG. 5, pro-health gene expression cluster scores and pro-health microbial taxa cluster scores can be used to provide an initial pro-health weight. Depending on, for example, the strength of the initial pro-health weight, this way can be modified using pro-health phenotype cluster scores to produce a pro-health component score ("x"—anti-inflammatory is considered pro-health). Similarly, anti-gene expression cluster scores and anti-microbial taxa cluster scores can be used to provide an initial anti-weight. Depending on, for example, the strength of the initial anti-weight, this way can be modified using anti-phenotype cluster scores to produce and anti-health component score ("y"—pro-inflammatory is considered anti-health). The pro-health and anti-health complement scores can be used to modify an initial health score. For example, an initial health score may be set at 5 on a 10 point scale. And anti-health component can lower the score while a pro-health component can increase the score.

V. Inferring Health Scores

The first and second computer models described above are useful for generating a health score for a health metric for a subject. In one embodiment raw data, as described above, is collected for subject. The data is processed to produce a data set that comprises data for each raw feature used by the first model to infer feature cluster scores. In a first operation, the first model infers feature cluster scores and generates a second data set including the scores. In a subsequent operation, the second model infers a health score for the health metric using the feature cluster scores in the second data set.

A biological sample and questionnaire data can be received from the subject. The sample in the questionnaire data can be analyzed to generate-omic information, for example microbiome transcriptomic information and phenotypic information. Other sources of information about a subject can come, for example, the subject's activity on social media. This data can then be subject to a two-step analysis process as described herein to generate one or more health scores. The health scores, with or without recommendations for improving health, can be communicated to the subject over a communications network to an electronic device accessible by the subject. Communication may be, for example, in the form of information provided on a password-protected website accessible by the subject. Alternatively, communication may be by email or text message. Electronic devices accessible by the subject can include, for example, computers connected to the Internet, smart phones (e.g., iPhone® or Samsung Galaxy®), or a wearable device (e.g., Fitbit® or Garmin®).

VI. Interventions

Health scores for health metrics can be used to recommend or provide interventions for subjects to improve their health scores. The desired result of an intervention is an improvement in a health score, e.g., toward a healthier score.

Interventions can include, without limitation, changes in lifestyle, such as diet, exercise, sleep, and stress reduction. Interventions also can include the administration of pharmaceuticals or probiotics, vitamins, minerals, herbal formulas and other nutraceuticals.

Probiotic interventions include, for example, probiotic organisms such as *Bifidobacterium bifidum, Bifidobacterium animalis, Bifidobacterium longum, Bifidobacterium infantis, Lactobacillus acidophilus, Lactobacillus casei, Lactobacillus lactic, Lactobacillus reuteri, Lactobacillus rhamnosus* GG, *Lactobacillus bulgaricus, Streptococcus thermophils*, and *Saccharomyces boulardii.*

Prebiotic interventions include, for example, products with fructooligosaccharides, galactooligosccharides, inulin, guar gum, chicory root, acacia fiber, and green banana flour.

Microbiome modulator interventions include, for example, polyphenol supplements including productions containing flavonoids, stilbene, lignans, phenolic acids, curcuminoids, and gingerols.

The intervention may include changes to diet and/or administration of supplements. Foods may be categorized in terms of their ability to improve or worsen a condition. Foods may be included in a food ontology. Exemplary foods that can be included in the food ontology include, for example, those listed in Table 1.

TABLE 1

| Exemplary Foods | | |
|---|---|---|
| Abalone | Almond Milk (unsweetened) | Artichoke |
| Acacia Gum | Almonds | Arugula |
| Adzuki Beans | Amaranth | Asparagus |
| Agar | Anchovy | Aspartame |
| Agave Nectar | Apple (medium, organic) | Avocado |
| Alfalfa Sprouts | Apricot | Avocado Oil |
| Allspice | Brown Sugar | Bamboo Shoots |
| Barley | Brussels Sprouts | Banana (small) |
| Basil | Buckwheat | Chicken (white) |
| Bay Leaf | Buffalo | Chickpeas |
| Beans (baked or | | Chicory (root) |
| | | Chili Powder |

TABLE 1-continued

| Exemplary Foods | | |
|---|---|---|
| refried) | Bulgur | Chlorella |
| Bean Sprouts | Burdock Root | Cilantro |
| Beef (fatty, | Butter | Cinnamon |
| grass-fed) | Cabbage | Cloves |
| Beef (lean, | Cane Sugar | Cocoa |
| grass-fed) | Canned | (unsweetened) |
| Beer | Vegetables | Coconut MCT Oil |
| Beet | Canola Oil | Coconut Meat |
| Beet Greens | Capers | Coconut Milk |
| Beet Sugar | Caraway Seed | (unsweetened) |
| Bell Pepper | Cardamom | Coconut Oil |
| (organic) | Cardoon (thistle | Coconut Water |
| Black Beans | stem) | Cod, Alaskan |
| Blackberry | Carob | Coffee (brewed, |
| Black Eyed Peas | Carrot | organic) |
| Black Pepper | Cashews | Collard Greens |
| Black Tea | Cassava | Coriander |
| (brewed) | Catfish | Cornish Game |
| Blueberry | Cauliflower | Hen |
| Bok Choy | Caviar or Roe | Corn Syrup |
| Bone Broth (fish) | Cayenne Pepper | Corn Tortilla |
| Bone Broth | Celeriac | (organic, non- |
| (mammal) | Celery (organic) | GMO) |
| Bone Broth | Celery Seed | Couscous |
| (poultry) | Chanterelle | Cranberry |
| Boston Beans | Mushrooms | Crayfish |
| Boysenberry | Chard | Cucumber |
| Brazil Nuts | Cheese | Cumin |
| Breadfruit | Cherry (organic) | Cured Meat |
| Broccoli | Chervil | Currant |
| Brown | Chestnuts | Curry Powder |
| Mushrooms | Chia Seeds | Daikon |
| Brown Rice | Chicken (dark) | Hydro- |
| Dandelion | Fruit Juices | genated |
| Greens | Game Meat | Vegetable Oil |
| Dates | (venison, elk) | Iodized Salt |
| Dextrose | Garlic | Jackfruit |
| Dill (fresh) | Ghee | Jerusalem |
| Duck | Ginger | Artichoke |
| Dungeness | Goat | Jicama |
| Crab, Pacific | Goat Cheese | Kale |
| Eel | Goat Milk | Kamut |
| Egg (large) | Goji Berry | Kasha |
| Eggplant | Goose | Kefir |
| Egg White | Gooseberry | Kimchi |
| Egg Yolk | Gourd | Kiwi |
| Elderberry | Granola Bars | Kohlrabi |
| Emu | Grapefruit | Kombucha |
| Endive | Grape Leaves | Kumquat |
| Enoki | Grape Seed Oil | Lamb |
| Mushrooms | Grapes (organic) | Lard |
| Escarole | Green Beans | Leek |
| Farro | Green Tea | Lemon |
| Fava Beans | (brewed) | Lentils |
| Fennel Bulb | Guava | Lettuce |
| Fennel Seed | Haddock | Lima Beans |
| Fenugreek Seed | Halibut, Pacific | Lime |
| Fermented | Hard Squash | Lobster |
| Vegetables | Heavy Cream | Loganberries |
| Fiddlehead | (33% fat) | Lo Han |
| Ferns | Hemp Hearts | Lotus Seeds |
| Fig | Herbal Tea | Lychee |
| Filberts | (brewed) | Maca |
| Filberts or | Herring | Macadamia Nuts |
| Hazelnuts | Hickory Nuts | Mace |
| Flax Oil | Honey | Mackerel |
| Flax Seeds | Horseradish | Maitake |
| Flounder | Hot Pepper | Mushrooms |
| Freekeh | (organic) | Maltose |
| French Fries | Huckleberry | Mango |
| Mangosteen | Parsnip | Radish |
| Manuka Honey | Passionfruit | Rainbow Trout |
| Maple Syrup | Peach | Raisins |
| Margarine | Peanuts | Raspberry |
| Marionberry | Pear (organic) | Red Beans |
| Marjoram | Peas | Red/Green/Rom |
| Melon | Pecans | aine Lettuce |
| Millet | Peppermint | Rhubarb |

TABLE 1-continued

| Exemplary Foods | | |
|---|---|---|
| Miso | (fresh) | Rice Cakes |
| Molasses | Perch | (flavored) |
| Morel | Persimmon | Rice Milk |
| Mushrooms | Pheasant | Rice Noodles |
| Mulberries | Pickle | Ricotta or |
| Mushrooms | (unsweetened) | Cottage Cheese |
| Mussel | Pineapple | (2% fat) |
| Mustard Greens | Pine Nuts | Rosemary (fresh) |
| Mustard Seed | Pinto Beans | Rutabaga |
| Natto | Pistachios | Rye (sprouted |
| Nectarine | Plantain | bread) |
| (organic) | Plum | Saccharin |
| Nutmeg | Pomegranate | Safflower Oil |
| Oatmeal | Poppy Seed | Saffron |
| (flavored) | Pork (lean) | Sage |
| Oats | Portabella | Salmonberry |
| Octopus | Mushrooms | Salmon, Pacific |
| Okra | Potato (small, | (wild-caught) |
| Olive Oil | organic) | Sardine |
| Olives | Processed | Sauerkraut |
| Onion | Cheese | Savoury |
| Orange | Processed Meat | Scallops |
| Oregano | Prunes | Scrod |
| Ostrich | Pummelo | Sea Salt or |
| Oyster | Pumpkin | Himalayan Salt |
| Mushrooms | Pumpkin Seeds | Seaweed (fresh) |
| Papaya | Quail | Sesame Seeds |
| Paprika | Quinoa | Sheep Cheese |
| Parsley | Radicchio | Sheep Milk |
| Shellfish Clam | Straw | Vinegar Apple |
| Shellfish Oyster | Mushrooms | Cider |
| Shitake | Sucralose | Walnuts |
| Mushrooms | Sugar (white) | Water Chestnuts |
| Shortening | Summer Squash | Watercress |
| Shrimp | Sunflower Seeds | Wheatgrass |
| (domestic) | Sweet Potato/ | Wheat (sprouted |
| Snap Peas | Yam | bread) |
| Soda (regular or | Swiss Chard | Whey |
| diet) | Tapioca | White Beans |
| Sole | Taro | White Flour |
| Sour Cherries | Tarragon | White Rice |
| Sour Cream | Tempeh | White Tea |
| Soybeans (non- | Thyme | (brewed) |
| GMO) | Tilapia | Whole Milk |
| Soy Milk | Tofu | Wild Rice |
| (unsweetened) | Tomato (organic) | Wine |
| Spearmint (fresh) | Triticale | Xanthan Gum |
| Spinach | Tuna (pole | Xylitol |
| (organic) | caught) | Yam or Sweet |
| Spirulina | Turbot | Potato |
| Sprouted Radish | Turkey (dark) | Yeast |
| Seeds | Turkey (white) | Yogurt (flavored) |
| Squid | Turmeric | Yogurt (plain) |
| Star Fruit | Turnip | Zucchini Squash |
| Stevia | Vanilla Extract | |
| Strawberry | Veal | |
| (organic) | Vinegar | |

The intervention also may include recommendations regarding administration of macronutrients and/or micronutrients. Macronutrients include, for example, carbohydrates, fiber (generally indigestible carbohydrates), proteins, and fats. Micronutrients include, for example, vitamins (e.g., water-soluble vitamins and fat-soluble vitamins) and minerals (e.g., macro minerals and trace minerals). Water-soluble vitamins include, for example, Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate), Vitamin B12 (cobalamin), and Vitamin C (ascorbic acid). Fat-soluble vitamins include, for example, vitamin A, vitamin D, vitamin E and vitamin K. Macro minerals include, for example, calcium, phosphorus, magnesium, sodium, chloride, potassium and sulfur. Trace minerals include, for example, iron, manganese, copper, zinc, iodine, fluoride and selenium.

The intervention also can include recommendations regarding administration of any of a variety of compounds. For example, the compounds can be those listed in Table 2.

TABLE 2

| Exemplary Specific Compounds | | |
|---|---|---|
| | | Absorbable Carbohydrate |
| Adenine Nutrient | Aglycone | Allergen Protein |
| Allicin | Alliin | Allyl Cysteine |
| Alpha Linolenic Acid | amino acids | Anethole |
| Anthocyanidin Nutrient | Anthocyanin | Apigenin |
| Arginine | Ascorbic Acid | Avenanthramide |
| Avenanthramide Nutrient | Avenanthramide Phenolic Acid | B carotene |
| B vitamins | Beta Carotene | Beta Glucan Cereal |
| Biotin | Butyrate | Butyric Acid |
| Caffeine | Caffeine Nutrient | Calcium |
| Calcium Ion2 | Capsaicin | Casein1 |
| Casein2 | Catechin | Cholesterol |
| Choline | Citrulline | Cobalamin |
| CoEnzymeQ10 | Collagen | Cyanidin |
| Cysteine | Daidzein | Delta-7-sterine |
| Deta-sitosterol | Dodecanoic Acid (Lauric Acid) | EGCG |
| EicosaPentanoic-Omega3 | ELLAGIC | Ellagic Acid |
| Epicatechin | Epigallocatechin Gallate | Essential fatty acids |
| Fatty Acid Nutrient_Omega3 | Fatty Acid Nutrient_Omega9 | ferulic acid |
| fiber | Flavonoid Nutrient | folate |
| folic acid | FOS | FructOligo-Saccharide |
| Fructose | GalactOligoSaccharide | GamaAmino-ButyricAcid |
| GammaAmino-ButyricAcid | GammaLinolenicAcid | gingerol |
| Gingerol Nutrient | GLA | Glucobrassicin |
| Glucoraphanin | GlucosinolateNutrient | glucosinolates |
| Glutamine | GLUTEN | GlycemicIndex |
| | GlycemicIndex/ Glycemic Load | glycoside |
| Guanine Nutrient | Hypoxanthine Nutrient | Inulin |
| iodine | Iodine Nutrient | iridoid glycoside |
| iron | IronIon2 | kampferol |
| Lactalbumin Alpha | Lactalbumin Beta | Lactose |
| lauric acid | Lectin | Lignan Nutrient |
| Limonin Glucoside | Linalool | Linoleic Acid |
| Lutein | Lutein Zeaxanthin | Luteolin |
| Lycopene | magnesium | Magnesium Ion2 |
| Maltose | Mannitol | medium chain triglycerides |
| Medium Chain Fatty Acid Nutrient | Mucilage | MUCIN |
| MUFAs | Naringenin | niacin |
| Nitrate | Nitrite | Oleic Acid |
| OXALATE | pantothenic acid | phospholipids |
| phosphorus | Phytonutrient Nutrient | phytonutrients |
| Phytosterol Nutrient | phytosterols | Polyphenol Nutrient |
| polyphenols | Polysaccharide Insoluble Fiber Nutrient | Polysaccharide Insoluble Nutrient |
| Polysaccharide Soluble Fiber Nutrient | Polysaccharide Soluble Nutrient | potassium |
| Potassium Ion | Potassium Ion1 | probiotics |
| protein | pyridoxine | Quercetin |
| Resistant Starch Nutrient | resveratrol | Retinoid Nutrient |
| riboflavin | S Adenosyl Methionine | Saponin Glycoside |
| Saponin Phytonutrient | saponins | Saturated Triacylglycerol Fat |
| selenium | Selenium Nutrient | Sesquiterpene Lactone |
| Sinigrin | sodium | SodiumIon1 |
| Sorbitol | Tannoid Nutrient | Theanine |
| Theobromine Nutrient | Theophylline Nutrient | thiamin |
| thiamine | thiols | Total Anthocyanidin |

TABLE 2-continued

| Exemplary Specific Compounds | | |
|---|---|---|
| | | Absorbable Carbohydrate |
| Total Carbohydrate By Difference Nutrient | Total Copper | Total Fiber Carbohydrate Nutrient |
| Total FructoOligosaccharide | Total GalactoOligosaccharide | Total Goitrogen |
| Total Inulin | Total Iron | Total Oxalate |
| Total Phosphorous | Total Polyphenol | Total Protein |
| Total Purine | Total Sulfur | Tryptophan |
| VitAIU | Vitamin C | Vitamin E |
| Vitamin A | Vitamin B12 | Vitamin B6 |
| Vitamin C | Vitamin D | Vitamin E |
| Vitamin K | VIT B | VITB2_Total Riboflavin |
| VITB3_Total Niacin | VITB5_Total Pantothenic Acid | VITB6_Total PLP |
| VITB9 | VITB9 Total Folate | VITE |
| VITK_TotalMK | Xanthine Nutrient | Zeaxanthin |
| Zinc | Zinc Ion2 | |

VII. Computer System

Health scores and recommendations can be provided to a subject in electronic or paper format. Data can be transmitted electronically, e.g. over the Internet. Electronic communication can be, for example, over any communications network include, for example, a high-speed transmission network including, without limitation, Digital Subscriber Line (DSL), Cable Modem, Fiber, Wireless, Satellite and, Broadband over Powerlines (BPL). Information can be transmitted to a modem for transmission e.g. wireless or wired transmission, to a computer such as a desktop computer. Alternatively, reports can be transmitted to a mobile device. Reports may be accessible through a subscription program in which a user accesses a website which displays the report. Reports can be transmitted to an electronic device accessible by the user. This could be, for example, a personal computer, a laptop, a smart phone or a wearable device, e.g. worn on the wrist.

Figure 6:
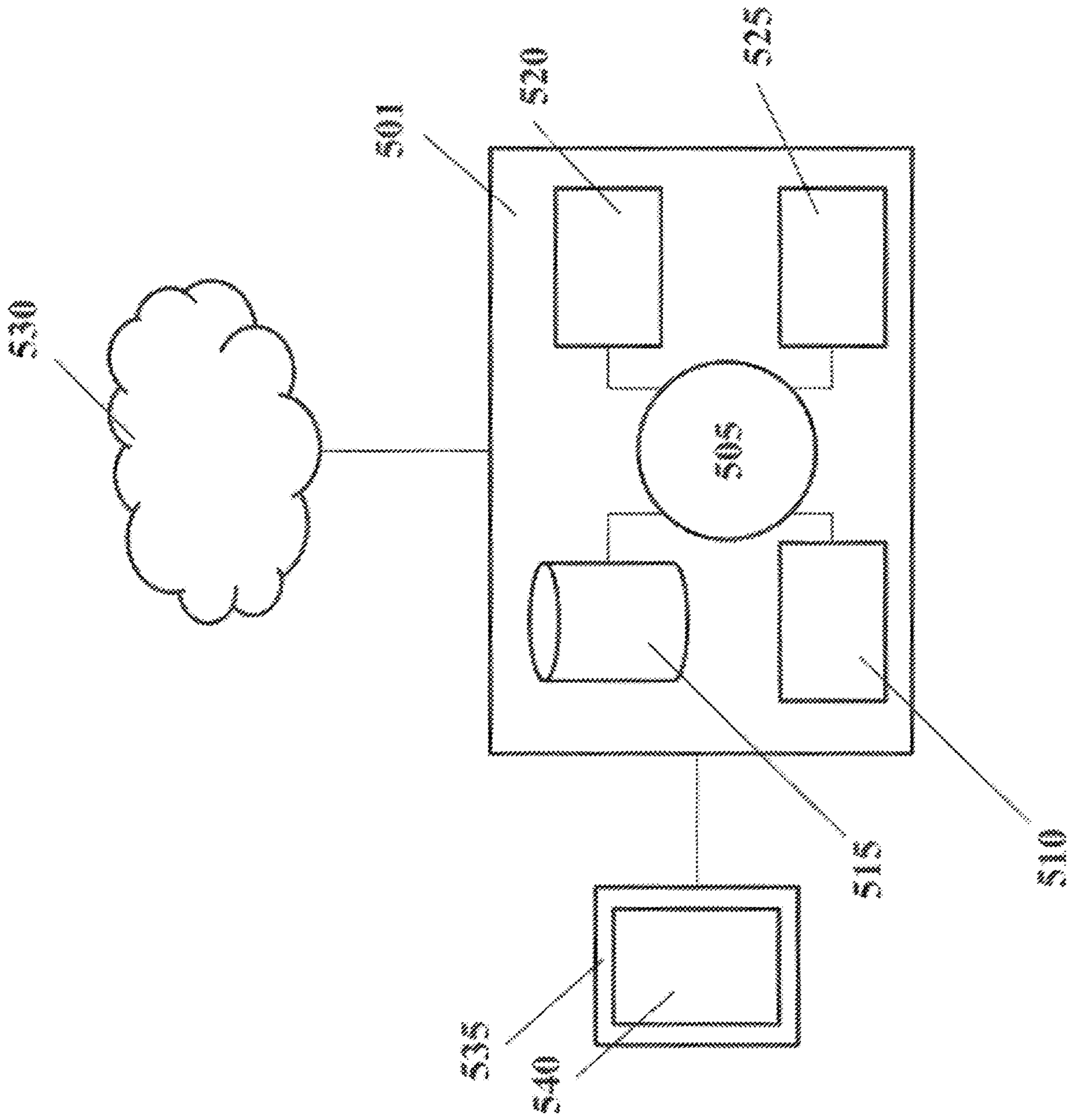
FIG. 6 shows an exemplary computer system.

FIG. 6 shows an exemplary processing system. The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure.

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530.

Methods as described herein can be implemented by way of machine (e.g., computer processor) executable code stored on an electronic storage location of the computer system 501, such as, for example, on the memory 510 or electronic storage unit 515. The machine executable or machine-readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks.

The computer system 501 can include or be in communication with an electronic display 535 that comprises a user interface (UI) 540 for providing, for example, input parameters for methods described herein. Examples of UIs include, without limitation, a graphical user interface (GUI) and web-based user interface.

EXAMPLES

I. Development of a Computer Model to Infer an Inflammation Score

Five-hundred subjects are enrolled in a study. Each subject provides responses to a questionnaire concerning phenotypic traits, and a stool sample. The responses are tabulated into a database. RNA from each stool sample is isolated. Non-informative RNA, such as ribosomal RNA and most abundant human messenger RNA species are removed from the sample. Remaining RNA is sequenced. Quantitative measures of microbial taxa in the RNA is determined using the GOTTCHA microbial taxonomy program. Quantitative measures of gene expression for more than 100 different genes are determined, in part, by mapping sequences from the meta-transcript on to an open reading frame database. These data are incorporated into the database. Together, this information represents data for each raw feature used in the inference process. Data for one hundred of the subjects is selected for preparing a first training data set. Data for the remaining four hundred subjects is reserved for use in a test data set.

A person skilled in the art (e.g., an expert) in the area of biological aspects of inflammatory conditions reviews the database and ranks each subject according to level of inflammation based on data for raw features grouped into feature clusters. The rankings are further included to the database to produce a first training data set.

A machine learning algorithm using decision tree analysis is trained on the first training data set to produce a feature cluster score model that infers feature cluster scores for each feature cluster.

The feature cluster score model is then used to infer feature cluster scores for each feature cluster in data in the test data set produced from data from the remaining four hundred subjects. The inferred feature cluster scores are assembled into a second database for producing a second training data set.

A second person skilled in the field of clinical aspects of inflammation who is different from the first person performs a partial order ranking of subjects in the second database for the Inflammatory Activity Health Metric based on the inferred feature cluster scores. This information is included in the second database to produce a second training data set.

A machine learning algorithm using decision tree analysis is trained on the second training data set to produce an inflammation score model that infers an inflammation score for a subject.

II. Inferring an Inflammatory Score for a Subject

A subject provides responses to a questionnaire about phenotype, and a stool sample. RNA from the stool sample is sequenced and levels of gene expression and amounts of microorganisms belonging to various taxa are calculated. The results are entered into a database as raw feature data.

A cluster score computer model and inflammatory score computer model, as described in a previous example are used to infer inflammatory score for the subject. The computer models infer that the subject has an inflammatory score of 9 on a scale of 1 to 10. Further analysis shows that the score is due to high levels of gene expression in genes in the butyrate and primary bile acids pathways, as well as high levels of proteobacteria, and as confirmed by subject-reported joint pain.

III. Subject Intervention

A computer generates a report for a subject indicating inferred scores for a number of different health metrics including inflammation, metabolic fitness, digestive efficiency, detox potential and gut neural balance. The report shows that the subject has an inflammatory score of 9, indicating high inflammation and a metabolic fitness score of 3, indicating somewhat slow metabolism. The report further includes recommendations for interventions to reduce inflammation. These recommendations include increased consumption of foods high in probiotics, fibers, and polyphenols. The report also includes recommendations for interventions to increase metabolism; these recommendations include increasing exercise to at least 10,000 steps per day and a diet low in carbohydrates and high in protein and fat. More specifically, the subject is recommended to eat, as "superfoods", bone broth, broccoli, cauliflower, spinach and parsley; and to avoid foods such as dextrose, maltose, maple syrup, margarine, molasses, raisins, triticale, wheat, white rice and xylitol.

The subject, exhibiting self-discipline, complies with recommendations. After three months the subject provides a new stool sample and new responses to the phenotype questionnaire. These data sources are analyzed as described above. Inflammatory score models and metabolic fitness score models indicate that the subject now has an inflammatory score of 6 and metabolic fitness score of 5.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one or more" and "one or a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

All publications, patents, and patent applications mentioned in this specification are herein incorporated by reference to the same extent as if each individual publication, patent, or patent application was specifically and individually indicated to be incorporated by reference.

What is claimed is:

1. A method that infers a health score for a health metric for a subject comprising:

(a) providing a first data set comprising, for the subject, feature data for each of a plurality of features selected from one or more feature groups;

(b) defining a plurality of feature clusters from the feature data, wherein each feature cluster in the plurality of feature clusters comprises a collection of features in the plurality of features;

(c) executing a first computer model on the first data set to assign feature cluster scores for the health metric to each of the plurality of feature clusters, wherein the first computer model comprises a first machine learning algorithm, wherein each feature cluster score is a quantitative measure, thereby generating a second data set comprising a plurality of feature cluster scores;

(d) executing a second computer model on the second data set comprising the plurality of feature cluster scores to infer a health score for the health metric for the subject, wherein the second computer model comprises a second machine learning algorithm;

(e) obtaining, from the second computer model, a health score for the health metric for the subject that indicates a severity of the health metric that is present in the subject, wherein the severity is higher than a lowest category of severity; and (f) administering, responsive to determining the health score for the subject indicating the severity of the health metric is higher than the lowest category of severity, an intervention to the subject to improve the health score, thereby reducing the severity of the health metric in the subject, wherein the health metric is inflammation, and wherein the intervention comprises increased consumption of one or more of probiotics, fibers, and polyphenols.

2. The method of claim 1, further comprising training the first computer model and the second computer model by a process comprising:

a) receiving into computer memory a first training set, wherein the first training data set comprises, for each of a plurality of subjects, (1) feature data for each of a plurality of features selected from one or more feature groups and (2) feature cluster labels for each of one or a plurality of feature clusters, b) with a computer processor, training the first machine learning algorithm on the first training data set, wherein the first machine learning algorithm develops the first model that infers cluster scores for each of a plurality of feature clusters;

c) with a computer processor, executing the first model on a test data set comprising, for each of a plurality of subjects, feature data for the features, to produce a cluster score data set comprising, for each of the plurality of subjects in the test data set, feature cluster scores for each of the plurality of feature clusters;

d) labeling each subject in the cluster score data set with a health label for the health metric to produce a second training data set; and e) with a computer processor, training the second machine learning algorithm on the second training data set to develop the second model that infers a health score for the health metric based on feature cluster scores.

3. The method of claim 2, wherein the feature cluster labels comprise partial order cluster rankings assigned by a first person skilled in the field.

4. The method of claim 3, wherein the health labels comprise partial order health rankings assigned by a second person skilled in the field.

5. The method of claim 1, wherein the subject is a human subject.

6. The method of claim 1, wherein the feature data comprises microbiome feature data and phenotype feature data.

7. The method of claim 1, wherein the feature groups comprise gene expression data, microbial taxa data and phenotypic data and the feature data includes at least:

(1) data on gene expression for each of a plurality of genes in a microbiome of the subject;

(2) microbiome taxa quantity data for a plurality of microbes in a microbiome of the subject; and (3) phenotypic data for a plurality of different phenotypic traits of the subject.

8. The method of claim 7, wherein the microbiome is a fecal microbiome.

9. The method of claim 7, wherein the gene expression data comprises metatranscriptome sequence information.

10. The method of claim 7, wherein the gene expression data comprises data on expression of at least any of 10, 50, 100, 150, 200, 500, or 1000 different genes.

11. The method of claim 7, wherein the gene expression data comprises data on expression of genes involved in pathways associated with the health metric.

12. The method of claim 7, wherein the microbiome taxa data comprises data on microbes belonging to at least any of 10, 50, 100, 150, 200, 500, or 1000 different taxa.

13. The method of claim 7, wherein the microbiome taxa data comprises data on one or more groups selected from bacteria, viruses, Archaebacteria, yeast, fungi, parasites and bacteria phages.

14. The method of claim 7, wherein the phenotypic data for the plurality of different phenotypic traits comprises subject responses to one or more phenotypic traits selected from the group consisting of: age, sex, weight, blood type, headaches, faintness, dizziness, insomnia, watery or itchy eyes, swollen, red or sticky eyelids, bags or dark circles under eyes, blurred or tunnel vision, not including near or far-sightedness, itchy ears, earaches, ear infections, drainage from ear, ringing in ears, hearing loss, stuffy nose, sinus problems, hay fever, sneezing attacks, excessive mucus formation, chronic coughing, gagging, need to clear throat, sore throat, hoarseness, loss of voice, swollen or discolored tongue, gums or lips, canker sores, acne, hives, rashes, dry skin, hair loss, flushing, hot flashes, excessive sweating, irregular or skipped heartbeat, rapid or pounding heartbeat, chest pain, chest congestion, asthma, bronchitis, shortness of breath, difficulty breathing, bloated feeling, nausea, vomiting, diarrhea, constipation, belching, passing gas, heartburn, intestinal pain, stomach pain, pain or aches in joints, arthritis, stiffness or limitation of movement, pain or aches in muscles, feeling of weakness or tiredness, binge eating, binge drinking, craving certain foods, excessive weight, compulsive eating, water retention, underweight, fatigue, sluggishness, apathy, lethargy, hyperactivity, restlessness, poor memory, confusion, poor comprehension, poor concentration, poor physical coordination, difficulty in making decisions, stuttering or stammering, slurred speech, learning disabilities, poor physical coordination or clumsiness, numbness or tingling in hands or feet, mood swings, anxiety, fear or nervousness, anger, irritability or aggressiveness, sadness or depression, frequent illness such as colds, frequent or urgent urination, genital itch or discharge, decreased libido and PMS.

15. The method of claim 1, wherein the feature clusters comprise a plurality of gene clusters, a plurality of microbial taxa clusters and a plurality of phenotype clusters.

16. The method of claim 1, wherein the feature cluster score is a quantity having a discrete or continuous range.

17. The method of claim 1, wherein the feature data is provided by:

(i) providing a biological sample from the subject comprising microbiota;

(ii) sequencing nucleic acids in the biological sample to produce sequence data; and (iii) determining data for gene expression and microbiome taxa quantities using the sequence data.

18. The method of claim 1, wherein the second computer model generates a positive health component and a negative health component and combines the components to produce the health score for the health metric.

19. The method of claim 1, wherein feature clusters comprise one or more of: pro-inflammatory gene expression, pro-inflammatory taxa amounts, anti-inflammatory gene expression, anti-inflammatory taxa amounts, and intestinal barrier insufficiency gene expression and intestinal barrier insufficiency taxa amounts.

20. The method of claim 1, further comprising obtaining a second health score for a second health metric for the subject, wherein the second health metric is metabolic fitness, and feature clusters comprise one or more of:

(i) gene expression in pathways selected from one or more of: secondary bile acid pathway, primary bile acid pathway, butyrate pathway, methanogenesis pathway, acetate pathway, propionate pathway, branch chain amino acid pathway, long chain fatty acid metabolism pathway and long chain carbohydrate metabolic pathway; and (ii) taxa clusters selected from one or more of: *Prevotella* (genus)/*Bacteroides* (genus) ratio, *Eubacterium rectale* (species), *Eubacterium eligens* (species), *Faecalibacterium prausnitzii* (species), *Akkermansia muciniphila* (species), metabolic-related probiotic species (functional group), *Roseburia* (genus), *Bifidobacterium* (genus), *Lactobacillus* (genus), *Clostridium butyricum* (species), *Allobaculum* (genus), Firmicutes (phylum)/Bacteroidetes (phylum) ratio, Lachnospiraceae (family), Enterobacteriaceae (family), *Ralstonia pickettii* (species), *Bilophila wadsworthia* (species).

21. The method of claim 1, wherein the first machine learning algorithm or the second machine learning algorithm use supervised methods selected from the group consisting of artificial neural networks, decision trees, random forests, discriminant analyses, linear classifiers, partial least squares (PLS) regression, principal components regression (PCR), mixed or random-effects models, non-parametric classifiers, support vector machines, and ensemble methods.

22. The method of claim 1, wherein the health score obtained from the second computer model indicates that the severity of the health metric that is present in the subject is actionable.

23. The method of claim 1, wherein the health score obtained from the second computer model is a discrete number on a scale from 1 to 10, and wherein the health score for the subject is from 4 to 6 or from 7 to 10.

24. A method comprising:

a) training a first machine learning algorithm on a first training data set, wherein the first training data set comprises, for each of a plurality of objects, (1) feature data for each of a plurality of features and (2) a feature cluster label for each of one or a plurality of feature clusters, wherein the plurality of feature clusters is defined from the feature data and each feature cluster in the plurality of feature clusters comprises a collection of features in the plurality of features, and wherein the first machine learning algorithm develops a first model that infers a cluster score for each of the feature clusters based on the feature data, wherein the cluster score is a quantitative measure;

b) executing the first model on a test data set comprising, for each of a plurality of objects, feature data for the features, to produce a cluster score data set comprising, for each of the plurality of objects in the test data set, a feature cluster scores for each of the feature clusters;

c) labeling each subject in the cluster score data set with a label for a categorical variable to produce a second training data set;

d) training a second machine learning algorithm on the second training data set to develop a second model that infers a label for the categorical variable based on feature cluster scores;

e) using the first model and the second model to obtain a label for the categorical variable for a test subject, wherein the label for the categorical variable is an indication of a severity of inflammation present in the test subject, wherein the severity is higher than a lowest category of severity; and f) administering, responsive to the label for the categorical variable for the test subject indicating the severity of inflammation is higher than the lowest category of severity, an intervention to the test subject to improve the label for the categorical variable, thereby reducing the severity of inflammation, wherein the intervention comprises increased consumption of one or more of probiotics, fibers, and polyphenols.

* * * * *